United States Patent
Galazyuk

(10) Patent No.: US 11,304,917 B2
(45) Date of Patent: Apr. 19, 2022

(54) TREATMENT OF TINNITUS USING GLUTAMATE RECEPTOR AGONISTS

(71) Applicant: Northeast Ohio Medical University, Rootstown, OH (US)

(72) Inventor: Alexander V. Galazyuk, Kent, OH (US)

(73) Assignee: NORTHEAST OHIO MEDICAL UNIVERSITY, Rootstown, OH (US)

( * ) Notice: Subject to any disclaimer, the term of this patent is extended or adjusted under 35 U.S.C. 154(b) by 855 days.

(21) Appl. No.: 15/999,753

(22) PCT Filed: Feb. 19, 2016

(86) PCT No.: PCT/US2016/018572
§ 371 (c)(1),
(2) Date: Aug. 20, 2018

(87) PCT Pub. No.: WO2017/142543
PCT Pub. Date: Aug. 24, 2017

(65) Prior Publication Data
US 2021/0251928 A1    Aug. 19, 2021

(51) Int. Cl.
*A61K 31/196* (2006.01)
*A61P 27/16* (2006.01)
(52) U.S. Cl.
CPC ............ *A61K 31/196* (2013.01); *A61P 27/16* (2018.01)

(58) Field of Classification Search
None
See application file for complete search history.

(56) References Cited

U.S. PATENT DOCUMENTS

| | | | |
|---|---|---|---|
| 2011/0263652 A1* | 10/2011 | Friedman | A61K 31/4523 514/333 |
| 2015/0313839 A1 | 11/2015 | Lichter et al. | |

OTHER PUBLICATIONS

International Search Report and Written Opinion dated May 3, 2016 for corresponding International Application No. PCT/US2016/018572.
Kostek et al., "A New Method for Measuring the Psychoacoustical Properties of Tinnitus", Diagnostic Pathology, 8:209, 2013 entire document.

* cited by examiner

*Primary Examiner* — Joseph R Kosack
(74) *Attorney, Agent, or Firm* — Tarolli, Sundheim, Covell & Tummino LLP

(57) ABSTRACT

A method of treating tinnitus in a subject is described that includes administering a therapeutically effective amount of a group II metabotropic glutamate receptor (mGluR) agonist to the subject. A method of screening a subject having tinnitus for treatment with a group II mGluR agonist that includes testing the use of residual inhibition to suppress tinnitus in the subject, wherein suppression of tinnitus by residual inhibition indicates that a group II mGluR agonist would be effective for treating tinnitus in the subject, is also described.

13 Claims, 16 Drawing Sheets

TREATMENT OF TINNITUS USING GLUTAMATE RECEPTOR AGONISTS

GOVERNMENT FUNDING

The present invention was made with Government support under Grant Nos. R01 DC011330 and 1F31DC013498-01A1 awarded by the National Institute on Deafness and Other Communication Disorders. The Government has certain rights in the invention.

RELATED APPLICATIONS

The present invention is a U.S. National Stage under 35 USC 371 patent application, claiming priority to Serial No. PCT/US2016/018572, filed on 19 Feb. 2016, the entirety of which is incorporated herein by reference.

BACKGROUND

Tinnitus is defined as the perception of sound when no external auditory stimulus is present. Almost all individuals experience this perceptual phenomenon for brief, unobtrusive periods. However, some individuals experience persistent pervasive and disturbing ringing, known as chronic tinnitus. Despite its ubiquity and morbidity, many details of the pathophysiology of tinnitus remain to be elucidated, and there is no generally accepted cure.

Over the course of the last few decades, tinnitus research has identified two major directions for alleviation of tinnitus. One direction combines direct and indirect brain stimulation including vagus nerve stimulation. Smit et al., Brain Res 1608:51-65 (2015). The other major direction utilizes habituation training to decrease tinnitus perception and tinnitus-induced reactions (Jastreboff P J, Neurosci Res 8:221-254 (1990)) or the use of external sounds to mask or suppress the perception of tinnitus. Hoare et al., J Am Acad Audiol 25:62-75 (2014). An external sound often acts as a distractor and usually decreases the relative distress from tinnitus. Schleuning A J, Johnson R M, Int Tinnitus J 3:25-29 (1997). Tinnitus can also be briefly eliminated/reduced after a masking stimulus has been terminated, the phenomenon known as residual inhibition (RI). This effect was first described by a physician named A. J. Spaulding when he was trying to match patients' tinnitus to various spectral properties using musical instruments. Spalding J A, Archives of Otology 32:263-272 (1903). However, it wasn't until much later that RI was first systematically investigated. Feldmann H, Audiology 10:138-144 (1971).

Importantly, about 80% of patients with tinnitus indicate some degree of residual inhibition (RI), brief suppression of tinnitus following an external sound. Roberts et al., Acta Otolaryngol Suppl 556:27-33 (2006). Although the duration of RI varies considerably among individuals ranging from several minutes to hours, the majority of patients experience suppression of tinnitus from 5 to 30 seconds. Roberts et al., J Assoc Res Otolaryngol 9:417-435 (2008). Current research has identified basic psychoacoustic properties of RI. Vernon J A, Meikle M B, Otolaryngol Clin North Am 36:293-305 (2003). The depth (magnitude of tinnitus reduction) and duration of RI largely depend on intensity, duration, and spectrum of the sound used to induce RI. A recent study of RI found that repetitive induction of RI leads to the reduction of its duration and depth. Sedley et al., Curr Biol 25:1208-1214 (2015). The mechanism of RI has been a subject of intense debate among researchers. Overall, RI constitutes a unique internal mechanism for temporary tinnitus suppression. Increased knowledge about this mechanism may not only shed light on the cause of tinnitus, but also may help to develop an effective tinnitus treatment.

In two recent studies conducted on bats and mice, it was found that brief sounds can trigger a long-lasting suppression of spontaneous firing in inferior colliculus neurons after sound cessation. Voytenko S V, Galazyuk A V, Neurosci Lett 492:145-149 (2011). Much like RI, the duration of this suppression increased with sound duration and sound intensity, although the sounds were much shorter than those used to induce RI in humans Since elevated spontaneous firing or hyperactivity in auditory neurons has been linked to tinnitus (Eggermont J J, Roberts L E, Front Syst Neurosci 6:53 (2012)), suppression of this hyperactivity with sound may be an underlying mechanism of RI.

Tinnitus, the perception of sound in the absence of an auditory stimulus, is perceived by about one in 10 adults, and for at least 1 in 100, tinnitus severely affects their quality of life. No curative treatments are available. However, tinnitus symptoms can be alleviated to some extent. The most widespread management therapies consist of auditory stimulation and cognitive behavioral treatment, aiming at improving habituation and coping strategies. Presently, there are no FDA- or EMEA-approved drugs for the treatment of tinnitus. Additionally, none of the investigated drugs have demonstrated to provide replicable long-term reduction of tinnitus impact in the majority of patients, in excess of placebo effects, during recent clinical trials. Langguth et al., Expert opinion on emerging drugs, 14(4):687-702 (2009). Lastly, the lack of effective medications has forced physicians to prescribe off-label therapies with questionable outcomes to their desperate patients.

Tinnitus is a common work-related disability, particularly common in industrial, manufacturing, and military settings. In fact, the "US Veterans Administration Benefits Report" ranked tinnitus as the second most prevalent service related disability. Among those who began receiving benefits in 2006, tinnitus was ranked first among service related disability, accounting for 9.7% of the total. In 2006, the annual compensation for tinnitus related disability was S536 million. The Royal Institute for Deaf People ("RNID") estimates that 13 million people in Western Europe and the USA currently seek medical advice for their tinnitus. Over 4 million prescriptions are written each year for tinnitus relief but these are all for off-label drugs from a wide variety of therapeutic classes and most are associated with considerable side effects. Accordingly, there remains a need for an effective method for treating tinnitus.

SUMMARY OF THE INVENTION

In one aspect, the present invention provides a method of treating tinnitus in a subject, that includes administering a therapeutically effective amount of a group II metabotropic glutamate receptor (mGluR) agonist to the subject. In some embodiments, the group II mGluR agonist is selected from the group consisting of (1S,3R)-ACPD, cis-ACPD, (±)-trans-ACPD, (2R,4R)-APDC, (S)-3-Carboxy-4-hydroxyphenylglycine, (S)-4-Carboxy-3-hydroxyphenylglycine, (S)-4-Carboxyphenyglycine, L-CCG-I, DCG IV, LY354740, LY379268, (±)-LY395756, MAP4, NPEC-caged-LY379268, and spaglumic acid, and pharmaceutically acceptable salts thereof. In a further embodiment, the group II mGluR agonist is LY354740 or an LY354740 prodrug.

Other embodiments incorporate other details. For example, in some embodiments, the subject is human, and a dose of LY354740 from about 100 to 200 mg/day is administered. In other embodiments, the group II mGluR agonist is administered systemically, while in yet further embodiments, the group II mGluR agonist is administered with a pharmaceutically acceptable carrier. In other embodiments, the tinnitus is subjective tinnitus, while in yet further embodiments administration of group II mGluR agonist provides treatment of tinnitus for at least 15 minutes following administration.

Another aspect of the invention provides a method of screening a subject having tinnitus for treatment with a group II metabotropic glutamate receptor (mGluR) agonist, that includes testing the use of residual inhibition to suppress tinnitus in the subject, wherein suppression of tinnitus by residual inhibition indicates that a group II mGluR agonist would be effective for treating tinnitus in the subject. In some embodiments, the use of residual inhibition to suppress tinnitus in the subject is tested by administering a masking stimulus using a sound synthesizer. In further embodiments, the method of screening includes administering a therapeutically effective amount of a group II mGluR agonist to a subject in which tinnitus is suppressed by residual inhibition. In yet further embodiments, the group II mGluR agonist being administered is LY354740 or an LY354740 prodrug.

BRIEF DESCRIPTION OF THE FIGURES

The present invention may be more readily understood by reference to the following figures, wherein.

DETAILED DESCRIPTION OF THE INVENTION

Figure 1:
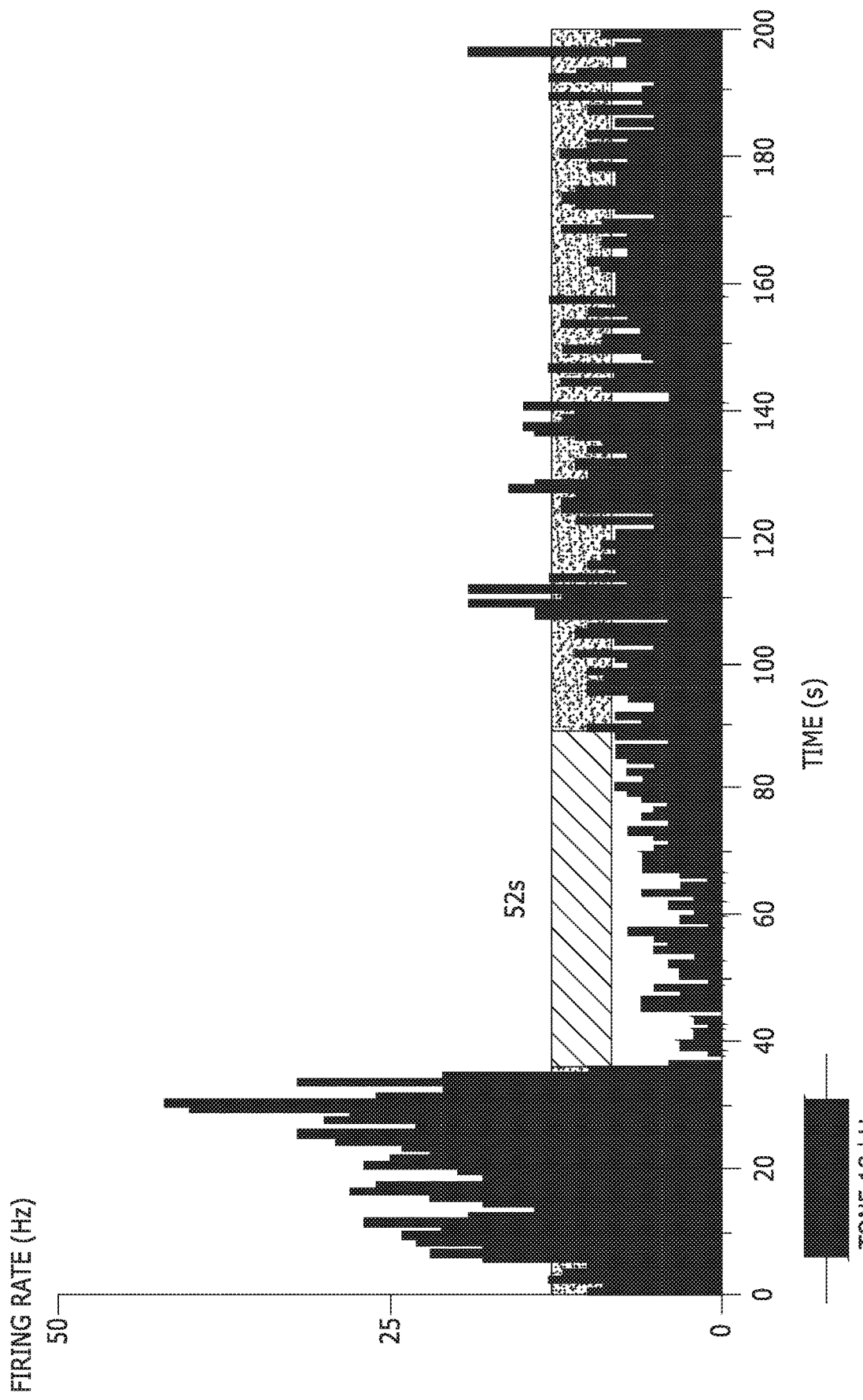
FIG. 1 provides a graph showing the long-lasting suppression of spontaneous firing in an inferior colluculus (IC) neuron following a sound stimulus. PSTH (peristimulus time histogram) of a single recording of an IC neuron in response to a pure tone (30 s duration) presented at the neuron's CF (18 kHz) at 70 dB SPL or 40 dB above the neuron's response threshold. Horizontal semitransparent bar represents an averaged level of spontaneous firing ±2 SD calculated based on spontaneous neuronal firing recorded during 5 s before the stimulus onset. The hashed bar indicates the duration of suppression (52 s, shown above). The sound stimulus is shown by a black horizontal bar below the histograms (same timescale as histogram). Bin size is 1 s.

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

Treat," "treating," and "treatment," etc., as used herein, refer to any action providing a benefit to a subject afflicted with a condition or disease such as tinnitus, including improvement in the condition through lessening or suppression of at least one symptom, delay in progression of the disease, prevention or delay in the onset of the disease.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, a "therapeutically effective amount" of a composition is that amount which is sufficient to show a benefit (e.g., a reduction in a symptom associated with the disorder, disease, or condition being treated) while avoiding adverse side effects such as those typically associated with alternative therapies. The therapeutically effective amount may be administered in one or more doses.

As used herein, the term "pharmaceutically acceptable carrier" refers to carriers that do not negatively affect the biological activity of the therapeutic molecule or compound to be placed therein. The characteristics of the delivery vehicle will depend on the route of administration. Therapeutic compositions may contain, in addition to the active compound, diluents, fillers, salts, buffers, stabilizers, solubilizers, and other materials well known in the art. A pharmaceutically acceptable carrier can deliver the type II mGluR agonists without unduly deleterious side effects in light of the severity of the disease and necessity of the treatment.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

A subject, as defined herein, is an animal, preferably a mammal such as a domesticated farm animal (e.g., cow, horse, pig) or a pet (e.g., dog, cat). More preferably, the subject is a human. The subject may also be a subject in need of treatment of a tinnitus.

In one aspect, the present invention provides a method of treating tinnitus in a subject. The method includes administering a therapeutically effective amount of a group II metabotropic glutamate receptor (mGluR) agonist to the subject. A wide variety of group II mGluR agonists are known to those skilled in the art. For a review of patented group II mGluR agonists, see Trabanco A. and Cid J, Expert Opin Ther Pat., 23(5), 629-47 (2013), the disclosure of which is incorporated herein by reference.

In some embodiments, the group II mGluR agonist is selected from the group consisting of (1S,3R)-ACPD, cis-ACPD, (±)-trans-ACPD, (2R,4R)-APDC, (S)-3-Carboxy-4-hydroxyphenylglycine, (S)-4-Carboxy-3-hydroxyphenylglycine, (S)-4-Carboxyphenylglycine, L-CCG-I, DCG IV, LY354740, LY379268, (±)-LY395756, MAP4, NPEC-caged-LY379268, and spaglumic acid, and pharmaceutically acceptable salts thereof. The full chemical names for these various group II mGluR agonists are described below.

The methods of treatment are capable of providing relief from tinnitus for a significant period of time. In some embodiments, administration of a therapeutically effective amount of the group II mGluR agonist provides relief from tinnitus for at least 5 minutes, at least 10 minutes, at least 15 minutes, at least 30 minutes, at least one hour, or at least two hours.

Type II mGluR Agonists

Glutamate receptors include ionotropic and metabotropic glutamate receptors, which mediate fast and slow neuronal actions, respectively. Eight members of the mGluRs have been identified, and have been divided into group I, group II, and group III receptors. Lu, Y., Neuroscience 274, 429-445 (2014). Type II mGluR agonists are compounds that bind to and activate type II metabotropic glutamate receptors.

A list of various abbreviations used for known type II mGluR agonists are provided, along with their full chemical names. This compounds listed here are exemplary, and are not meant as a comprehensive list of all type II mGluR agonists available. Examples of type II mGluR agonists include (1S,3R)-ACPD: (1S,3R)-1-Aminocyclopentane-1, 3-dicarboxylic acid; cis-ACPD: (±)-1-Aminocyclopentane-cis-1,3-dicarboxylic acid; (±)-trans-ACPD: (±)-1-Aminocyclopentane-trans-1,3-dicarboxylic acid; (2R,4R)-APDC: (2R,4R)-4-Aminopyrrolidine-2,4-dicarboxylate; (RS)-3,4-DCPG: (RS)-3,4-Dicarboxyphenylglycine; L-CCG-I: (2S, 1'S,2'S)-2-(Carboxycyclopropyl)glycine; DCG IV: (2S,2'R, 3'R)-2-(2',3'-Dicarboxycyclopropyl)glycine; E4CPG: (RS)-α-Ethyl-4-carboxyphenylglycine; LY354740: (1S,2S,5R, 6S)-2-Aminobicyclo[3.1.0]hexane-2,6-dicarboxylic acid; LY379268: (1R,4R,5S,6R)-4-Amino-2-oxabicyclo[3.1.0] hexane-4,6-dicarboxylic acid; LY341495: (2S)-2-Amino-2-[(1S,2S)-2-carboxycycloprop-1-yl]-3-(xanth-9-yl) propanoic acid; (±)-LY395756: (1S,2S,4R,5R,6S)-re1-2-Amino-4-methylbicyclo[3.1.0]hexane-2,6-dicarboxylic acid; MAP4: (S)-2-Amino-2-methyl-4-phosphonobutanoic acid;

NPEC-caged-LY379268: (N)-1-(2-Nitrophenyl)ethylcarboxy-(1R,4R,5S,6R)-4-Amino-2-oxabicyclo[3.1.0]hexane-4,6-dicarboxylic acid; (RS)-MCPG disodium salt: ((RS)-α-Methyl-4-carboxyphenylglycine disodium salt; spaglumic acid: N-Acetyl-L-aspartyl-L-glutamic acid.

In some embodiments, the group II mGluR agonist is LY354740 or an LY354740 prodrug. LYS354740 was developed by Eli Lilly under the name Eglumegad as a treatment for anxiety. The drug was not advanced beyond a Phase 2 clinical trial as they did not show treatment effects of placebo. Identifying a promising drug candidate that has shown success in Phase 1 is very encouraging, since this indicates that the safety of the drug has been established. A variety of prodrug forms for excitatory amino acids, including LY354740, are described in U.S. Pat. No. 7,038,077, the disclosure of which is incorporated herein by reference. For example, in some embodiments, the prodrug LY544344 [(1S, 2S, 5R, 6S)-2-[(2'S)-(2'-amino)propionyl]aminobicyclo[3.1.0]hexane-2,6-dicarboxylic acid hydrochloride] can be used. Rorick-Kehn et al., J Pharmacol Exp Ther. 316(2), 905-13 (2006).

Tinnitus

The present invention provides a method of treating tinnitus in a subject. Tinnitus is the hearing of sound when no external sound is present. While often described as a ringing, it may also sound like a clicking, hiss, buzzing, whistling, or roaring, and in some cases unclear voices or music are heard. The sound may be soft or loud, low pitched or high pitched and appear to be coming from one ear or both, and can be either intermittent or continuous.

There are a wide variety of causes for tinnitus, including chronic noise damage, acute explosion injuries of the auditory system, acute hearing loss, and other diseases associated with a hearing loss. Inner ear hearing loss in a chronically advancing form or in form of a noise induced hearing loss, followed by acute hearing loss are, according to clinical studies, connected to tinnitus for more than two-thirds. Tinnitus appears to typically be the result of neuronal dysfunction within the auditory pathway. However, in many cases, despite an intensive analysis, a definite cause of tinnitus cannot be found.

Tinnitus includes both objective tinnitus, and subjective tinnitus. Subjective tinnitus is the most frequent type of tinnitus, and in some embodiments, the present invention is directed to treatment of subjective tinnitus. It can have many possible causes but, most commonly, results from hearing loss. A frequent cause of subjective tinnitus is noise exposure which damages hair cells in the inner ear causing tinnitus. Subjective tinnitus can only be heard by the affected person. Objective tinnitus, on the other hand, can be detected by other people and is usually caused by myoclonus or a vascular condition, although in some cases, tinnitus is generated by a self-sustained oscillation within the ear.

Protocols for diagnosis of tinnitus are known to those skilled in the art. Audiometric tests are first conducted in which the subjects are tested for hearing at various frequencies (e.g., 0.25, 0.5, 1, 2, 3, 4, 6, and 8 KHz). The basic test protocol for diagnosis of tinnitus involves measurement of four tinnitus parameters: (1) pitch, (2) loudness, (3) maskability, and (4) residual inhibition. Testing can be done using a Tinnitus Synthesizer. See for example the "Tinnitus Clinic Test Protocol," provided by the Oregon Health & Science University, and described on their website.

Screening Methods

Another aspect of the invention provides a method of screening a subject having tinnitus for treatment with a group II metabotropic glutamate receptor (mGluR) agonist. The method includes testing the use of residual inhibition to suppress tinnitus in the subject, wherein suppression of tinnitus by residual inhibition indicates that a group II mGluR agonist would be effective for treating tinnitus in the subject. Screening, as used herein, refers to the procedure for distinguishing subjects having tinnitus that are susceptible to treatment with a group II mGluR agonist from subjects having tinnitus who will likely not benefit from treatment with a group II mGluR agonist.

While not intending to be bound by theory, the method of screening is based on the discovery by the inventors that the mechanism through which residual inhibition is effective for suppressing tinnitus appears to be the same mechanism through which use of group II mGluR agonists are effective. The inventors found that suppression of spontaneous neuronal activity after a sound stimulus explains why tinnitus patients experience the phenomenon of residual inhibition, a brief suppression of tinnitus after a sound stimulus. If suppression of spontaneous activity by a sound eliminates tinnitus, then suppression of this activity with group II mGluR agonist LY354740 should also eliminate tinnitus in humans who experience residual inhibition. Accordingly, a test for residual inhibition can be used to determine if a group II mGluR agonist would be likely to be effective for treating tinnitus in the subject.

Residual inhibition, as described herein, is the phenomenon by which tinnitus can (typically) temporarily be eliminated or reduced after a masking stimulus has been administered. If you play a specific pulse of sound to a subject with tinnitus, in most cases you can reduce, or even silence, their tinnitus for a period of time after the pulse has stopped. Residual inhibition involves administering a masking sound to the subject.

Masking sounds can be produced by using sound synthesizer, a computer using software such as that provided by Tinnitus Masker Pro™, recordings on fixed medium such as CDs, or any other suitable means for reproducing the masking sound. In some embodiments, the use of residual inhibition to suppress tinnitus in the subject is tested by administering a masking stimulus using a sound synthesizer. A variety of sound synthesizers, also referred to as masking devices, are known to those skilled in the art. See Vernon J. and Meikle, M, Otolaryngol Clin N. Am 36, 307-320 (2003), the disclosure of which is incorporated herein by reference, for description of a variety of masking devices. Masking sounds should be tuned to the pitch range of the person's tinnitus to have the most effect. That pitch range is generally found within the pitch range of their hearing loss. To be effective, the masking sound must have sufficient volume and duration, and it should be played into the ear (or ears) in which the tinnitus is present. For additional information on methods to conduct residual inhibition, see the Tinnitus Clinic report. Vernon J. A., Meikle M. B., Ciba Foundation Symposium 85—Tinnitus, John Wiley & Sons, Chichester, UK, 239-262 (1981), the disclosure of which is incorporated herein by reference.

In further embodiments, the screening method includes administering a therapeutically effective amount of a group II mGluR agonist to a subject in which tinnitus is suppressed by residual inhibition. In other words, in these embodiments, the screening serves as a precursor to actual treatment. Treatment can involve use of any of the group II mGluR agonists described herein, as well as other treatments used for tinnitus, such as residual inhibition, relaxation therapy, biofeedback, hypnotherapy, iontophoresis, or lidocaine administration. In some embodiments, the group II mGluR agonist is LY354740 or an LY354740 prodrug.

Administration and Formulation

The pharmaceutical compositions of the present invention comprise a type II mGluR agonist, or pharmaceutically acceptable salts thereof, as the active ingredient, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The term "composition," as in pharmaceutical composition, is intended to encompass a product comprising the active ingredient (i.e., the group II mGluR agonist), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The present compounds can be combined as the active ingredient in intimate admixture with a pharmaceutically acceptable carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The present compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethypiperideine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the type II mGluR agonist is a basic compound, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

The data obtained from the cell culture assays and animal studies can be used in formulating a range of dosage for use in humans. The dosage may vary depending upon the dosage form employed and the route of administration. A dose may be formulated in animal models to achieve a circulating plasma concentration range that includes the $IC_{50}$ (i.e., the concentration of the test compound which achieves a half-maximal inhibition of symptoms). Such information can be used to more accurately determine useful doses in humans Levels in plasma may be measured, for example, by high performance liquid chromatography.

A therapeutically effective amount of type II mGluR agonist ranges from 0.001 to 30 mg/kg body weight, preferably 0.01 to 25 mg/kg body weight, more preferably 0.1 to 20 mg/kg body weight, and even more preferably 1 to 10 mg/kg, 2 to 9 mg/kg, 3 to 8 mg/kg, 4 to 7 mg/kg, or 5 to 6 mg/kg body weight. The type II mGluR agonist can be administered one time per week for between 1 to 10 weeks, preferably between 2 to 8 weeks, more preferably between 3 to 7 weeks, and even more preferably for 4, 5, or 6 weeks. The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of a type II mGluR agonist can include a single treatment or, preferably, can include a series of treatments.

Further information on therapeutically effective amounts of type II mGluR agonists (e.g., LY354740) are known to those skilled in the art based on prior trials involving use of LY354740 to treat other conditions such as panic disorder. See Bergink et al., Int Clin Psychopharmacol., 291-3 (2005). For example, when the subject is human, a dosage of from 50 to 500 mg, from 100 to 200 mg, or from 125 to 175 mg a day can be administered.

Examples have been included to more clearly describe a particular embodiment of the invention and its associated cost and operational advantages. However, there are a wide variety of other embodiments within the scope of the present invention, which should not be limited to the particular examples provided herein.

EXAMPLES

Example 1: Long-Lasting Suppression of Spontaneous Firing in Auditory Neurons: Implication to the Residual Inhibition of Tinnitus The inventor tested neurons in the central auditory system of the mouse with stimuli akin to those used to induce residual inhibition (RI), to determine the relationship between the characteristics of sound-triggered suppression and the psychoacoustic properties of RI. It was shown that the basic characteristics of suppression are similar to the psychoacoustic properties of the RI in humans, suggesting that suppression is indeed an underlying mechanism of RI. Interestingly, however, both normal animals and animals with behavioral signs of tinnitus exhibited long-lasting suppression. Thus suppression may constitute a normal sound processing phenomenon in the auditory system which in tinnitus patients allows an RI-induced alleviation of their symptoms.

EXPERIMENTAL PROCEDURES

Subjects

Adult male CBA/CaJ mice were used in this study. Mice were obtained from Jackson Laboratories and were approximately 12 weeks old with a mean weight of 27.5 g at the beginning of testing. Mice were housed in pairs within a colony room with a 12-h light-dark cycle (8 A.M. to 8 P.M.) at 25° C. All procedures used in this example were approved by the Institutional Animal Care and Use Committee at Northeast Ohio Medical University.

Extracellular Recording 48 mice from the control and 16 from the sound exposed tinnitus groups were used for extracellular recordings. Each mouse was anesthetized using isoflurane inhalation (1.5-2.0%, isoflurane administered by a precision vaporizer) prior to surgery. A midline incision of the skin over the cranium was made. The tissue overlying the skull then was removed and a small metal rod was glued to the skull using glass ionomer cement (3M ESPE, Germany). Following surgery, animals were allowed to recover for 1-2 days in individual holding cages.

Two days after surgery each mouse was trained to stay inside a small plastic tube, to be used as a holding device during recording sessions. The metal rod on the head of the mouse was secured to a small holder designed to restrain the head of the animal without causing distress, while the ears were unobstructed for free-field acoustic stimulation. Recordings were made from the inferior colluculus (IC) or auditory cortex (AC) in awake mice inside a single walled sound attenuating chamber (Industrial Acoustics Company, Inc). Throughout the recording session (3 to 4 hours), the animal was offered water periodically and monitored for signs of discomfort. After a recording session, the exposed skull was covered with sterile bone wax, and the animal was returned to its holding cage. Experiments were conducted every 2-3 days for a maximum of 2 weeks. No sedative drugs were used during recording sessions. If the animal showed any signs of discomfort, the recording session was terminated and the mouse was returned to its cage.

A small hole (~50 μm) penetrating the dura was drilled in the skull overlying the IC, through which a recording electrode was inserted into the IC or AC. Extracellular single-unit recordings were made with quartz glass micropipettes (10-20 MΩ impedance, 2-3 μm tip) filled with 0.5 M sodium acetate. The electrode was positioned into the drilled hole by means of a precision (1 μm) digital micromanipulator (Sutter, MP-285) using a surgical microscope (Leica MZ9.5). The relative position of each electrode was monitored from the readouts of digital micrometers using a common reference point on the skull. Vertical advancement of the electrode was made by a precision piezoelectric microdrive (Model 660, KOPF Instr.) from outside the sound attenuating chamber. Recorded action potentials were amplified (Dagan 2400A preamplifier), monitored audiovisually on a digital oscilloscope (DL1640, YOKOGAWA), digitized and then stored on a computer hard drive using EPC-10 digital interface and PULSE software from HEKA Elektronik at a bandwidth of 10 kHz.

Electrophysiology Data Analysis

Each neuron characteristic frequency, the frequency to which a given neuron responded with the lowest threshold, was determined manually by presenting pure tone stimuli at a wide range of frequencies intensities. The response threshold was defined as the minimum level required to evoke a response to 50% of the same stimulus presented multiple times. To determine the duration of suppression of the spontaneous firing elicited by sound stimuli, the spontaneous firing rates 5 seconds before and after the stimulus were measured and compared. Changes in firing rates were difficult to assess from PSTHs, thus we measured these changes over a 1 second sliding window. The window of analysis was initially aligned with the 0 ms point on the time axis of the PSTH and was shifted by 1 s increments until the end of the recording trace. Each point on the histograms in FIGS. 1, 2, 4-9 was aligned with the start time of the analysis window. The 5 seconds preceding a stimulus was used to compute the mean value for spontaneous firing rate. Suppression or in some cases facilitation of spontaneous firing was defined as the time interval following stimulus presentation that the spike rate was continuously less or more than two standard deviations below the spontaneous rate (95% confidence limits) recorded before the sound stimulus.

Acoustic Trauma

Mice were anesthetized with an intramuscular injection of a ketamine/xylazine mixture (100/10 mg/kg). An additional injection (50% of the initial dose) was given 30 min after the initial injection. Mice were unilaterally exposed to a one octave narrow-band noise centered at 12.5 kHz (~8-17 kHz). This noise was generated using a waveform generator (Tektronix AFG 3021B), amplified (QSC RMX 2450) to 116 dB SPL, and played through a speaker (Fostex T925A Horn Tweeter). The outputs of the loudspeaker were calibrated with a 0.25-in. microphone (Brüel and Kjaer 4135) attached to a measuring amplifier (Brüel and Kjaer 2525) and found to be ±4 dB between 10 and 60 kHz. During exposure the speaker was located ~10 cm from the animal's right ear. During exposure the left external ear canal was obstructed with a cotton plug and a Kwik-Sil silicone elastomer plug (World Precision Instruments).

Behavioral Assessment of Tinnitus

Mice were assessed for tinnitus 3 months after exposure. The ability of mice to detect a gap of silence preceding the startle stimulus was determined using commercial hardware/software equipment from Kinder Scientific, Inc. Mice were placed in a small restrainer situated on a plate with a pressure sensor. Any animal motion was detected by the sensor which measured its amplitude and stored data on the computer hard drive. Kinder Scientific software was used to generate a sequence of stimulus trials including a startle stimulus presented alone (STARTLE) and a startle stimulus paired with a gap (GAP+STARTLE) embedded into continuous background noise. The background consisted of narrow-band (⅓ octave) noise centered at six different frequencies (10, 12.5, 16, 20, 25, and 31.5 kHz). This background noise level was constant (60 dB SPL) throughout the session. The startle stimulus was white noise presented at 110 dB SPL, and lasted 20 ms. The gap of silence was 20 ms long and was presented 100 ms before (onset to onset) the startle stimulus.

For the gap detection test, parameters of our stimulus paradigm were set to levels which are typical for assuring a robust ~30% reduction in startle response amplitude caused by a preceding gap of silence in an otherwise continuous background sound.

The testing session started with an acclimation period lasting 3 min Immediately afterwards, animals received 10 STARTLE-only trials in order to habituate their startle responses to a steady state level. For each of six background frequencies, we presented five STARTLE only trials and five GAP+STARTLE trials. The STARTLE and GAP+STARTLE trials were pseudo-randomized. The inter-trial intervals were also pseudo-randomized between 7 and 15 s. After we completed testing all six background frequencies, the entire session was repeated one more time. Thus, during this testing for each background frequency, the total of 10 GAP+STARTLE trials and 10 STARTLE only trials were presented.

Tinnitus Data Analysis

All waveforms collected during testing sessions were analyzed offline using a recently developed automatic method of startle waveform identification via a template matching paradigm. Grimsley et al., J Neurosci Methods 253:206-217 (2015). Based on this separation, only trials that resulted in startle responses were included in the data analysis. A mathematical approach was used to normalize startle response magnitudes of individual animals to their body mass. This mathematical conversion has two benefits: first, the procedure normalizes for mass, allowing legitimate comparisons between animals of different mass and inter-animal comparisons over time with differing masses, and second, it converts the forces sensed by the piezoelectric startle plate into a more readily understandable unit of distance jumped: the center of mass displacement.

Startle responses showed some variability during the recording sessions: some animals sometimes exhibited an extremely strong startle response or did not startle at all. Therefore, the data in each session were statistically analyzed to remove outliers (Grubbs' test for outliers). For each background frequency, a total of 10 GAP+STARTLE trials and 10 STARTLE only trials were presented. To calculate the GAP+STARTLE/STARTLE ratio we calculated the mean for all STARTLE values. They changed little within one session. Then we divided each of 10 GAP+STARTLE values for a given background frequency by the startle mean value. These 10 ratio values at a given frequency were used to calculate mean and SD values. A one-way analysis of variance (ANOVA) was used to test for differences within a subject. The criterion for the presence of behavioral evidence of tinnitus was a significant reduction in gap detection performance at one or several background frequencies compared to the pre-exposure values. During the data analysis, the inventor found empirically that the 95% confidence interval is an optimal must-reach criterion to demonstrate changes in gap or prepulse detection performance induced by sound exposure.

Results

Long-Lasting Suppression of Firing Activity in IC Neurons

Extracellular responses to long-lasting sound stimuli (5 s or 30 s duration) were recorded from 201 IC neurons in 42 awake mice. The majority of neurons (87%, 175/201) exhibited spontaneous activity with firing rates ranging from 0.2 to 36 spikes per second (sp/s). Since the focus of this study was to examine the effects of sound stimuli on spontaneous activity, the inventor excluded neurons which did not exhibit spontaneous activity from the data analysis. More than one third of spontaneously active neurons (39.5%, $69/175$) exhibited suppression of their firing following sound stimulus termination. The remaining spontaneously active neurons (106/175) either showed suppression only during sound presentation (37/106) or no suppression at all (69/106). An extracellular response trace of a representative IC neuron exhibiting extended suppression is shown in FIG. 1.

This neuron had a spontaneous firing rate of 10.9 sp/s before a stimulus was presented. During the stimulus presentation its firing rate was increased to 28 sp/s. After the stimulus, neuronal firing was suppressed for about 52 seconds and then returned to the pre-stimulus level.

The suppression was highly sensitive to sound stimulus parameters. Changes of stimulus duration, spectrum or how the stimulus was presented could alter suppression duration or even reverse it into firing rate facilitation. Each of these stimulus-dependent effects are demonstrated below.

Effect of Sound Duration on Suppression Duration

Figure 2:
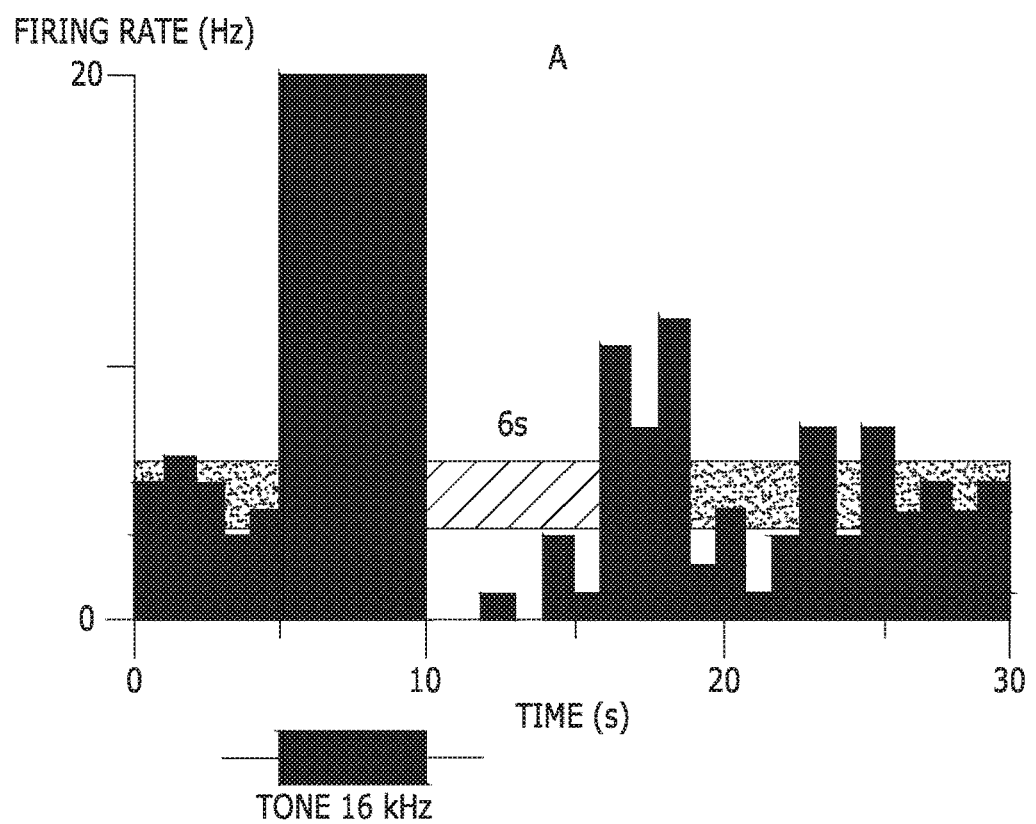
FIGS. 2A and 2B provide graphs showing the suppression duration of spontaneous firing in an IC neuron increases with sound stimulus duration. PSTH of a single recording of an IC neuron in response to a pure tone of 5 s (A) and 30 s (B) duration presented at the neuron's CF (16 kHz) at 65 dB SPL or 40 dB above the neuron's response threshold. The duration of suppression was 6 s in A and 38 s in B.
Figure 2:
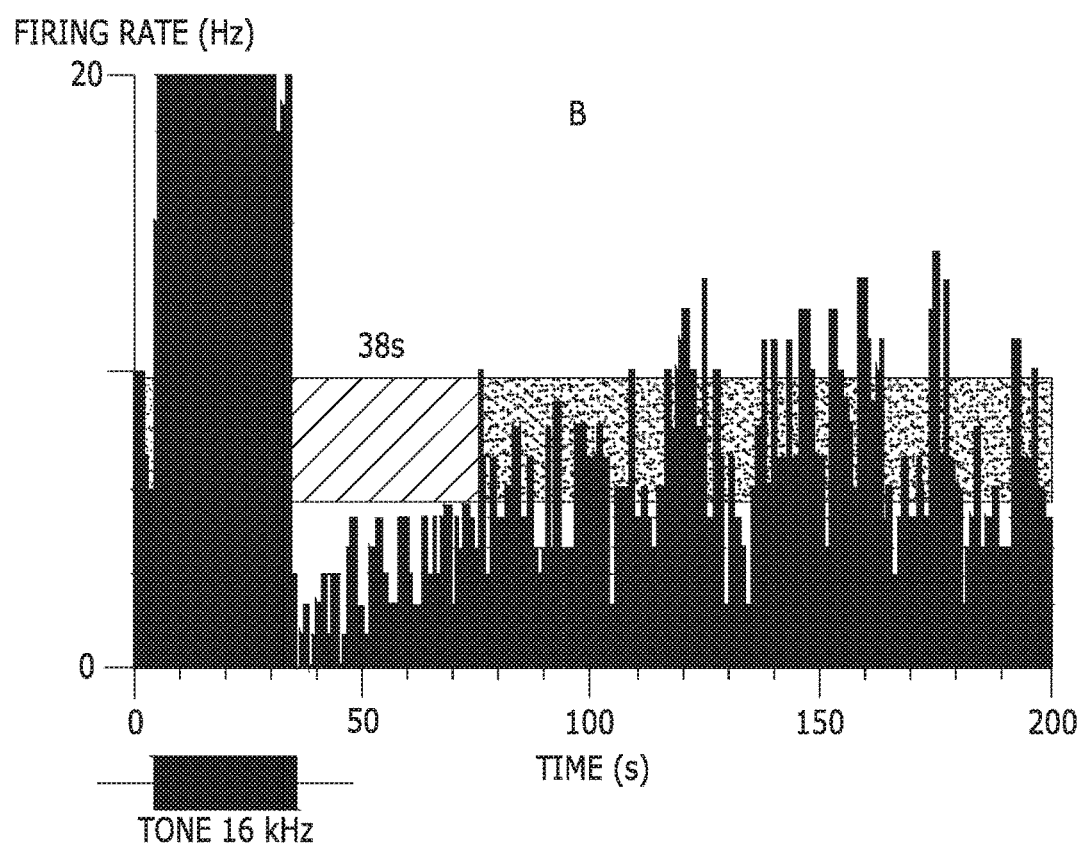

In agreement with our previous findings obtained in bats (Voytenko S V, Galazyuk A V, Neurosci Lett 492:145-149 (2011)), increasing the duration of the sound stimulus correspondingly prolonged suppression of spontaneous firing in IC neurons in mice. A representative neuron in FIG. 2 showed suppression lasting about 6 s in response to a pure tone of 5 s duration presented at the neuron's characteristic frequency (CF), the frequency at which a given neuron responds to the smallest sound intensity. When the sound duration was increased to 30 s this neuron exhibited suppression for ~38 s.

Figure 3:
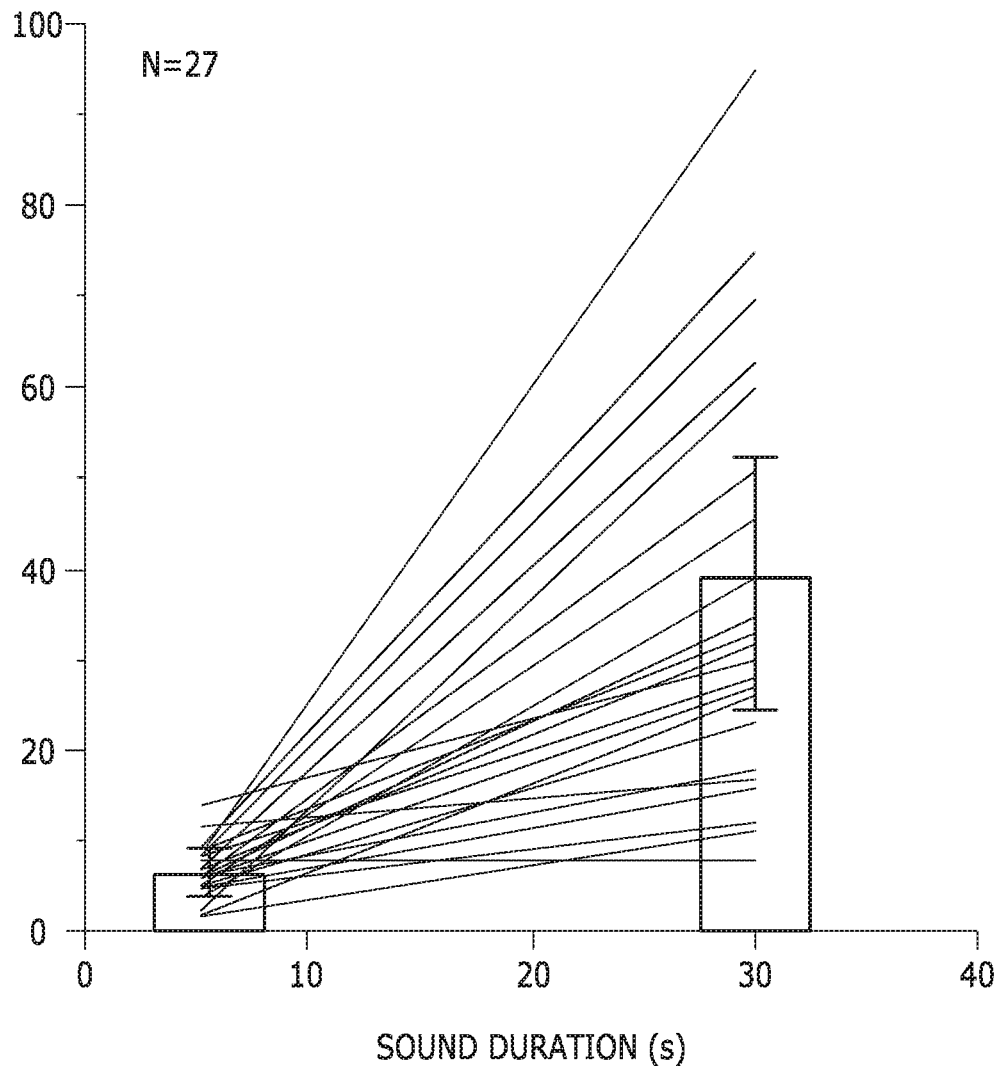
FIG. 3 provides a graph showing the duration of the suppression correlates with sound duration (r=0.71, p<0.0001). Suppression in 27 IC neurons was determined in response to both the 5 s and 30 s sound duration.

The population data on the IC neurons (27 units) which were tested with both 5 s and 30 s sound duration showed that the average duration of the suppression was roughly correlated with the sound duration; 5.8 s and 37.7 s, respectively (FIG. 3). However, some neurons demonstrated suppressions which exceeded the stimulus duration two or even three times.

Effect of Stimulus Spectrum on Suppression Duration

Figure 4:
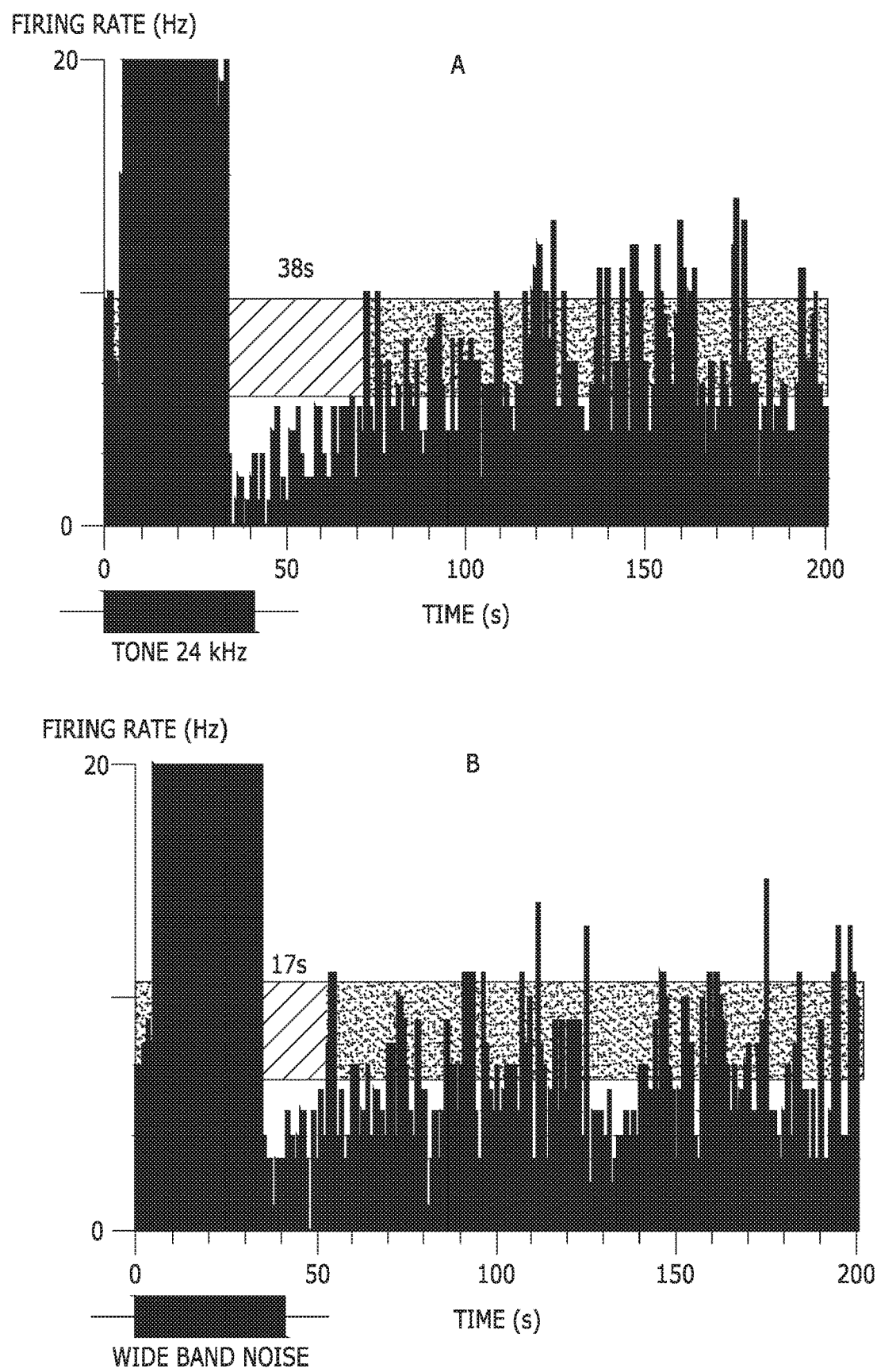
FIGS. 4A and 4B provide graphs showing the duration of suppression in IC neurons in response to a pure tone at the neurons' CF is longer than in response to a wideband noise. (A) PSTH of a single recording of an IC neuron to a 30 s pure tone at neuron's CF (24 kHz) presented at 65 dB SPL or 40 dB above threshold. (B) PSTH of the same neuron in response to a wideband noise. To compensate for the power loss the wideband noise was presented 10 dB louder (75 dB SPL). The duration of suppression was 38 s in A and 17 s in B. See legend of FIG. 1 for other details.

IC neurons showed responses to both pure tones and wide-band noises. We investigated whether the suppression in IC neurons was dependent on the spectral characteristics of the sound stimulus. The inventor found that pure tones presented at the neuron's CF were more effective in triggering a sustained suppression than noise stimuli (FIG. 4). The average duration of suppression from 12 IC neurons presented with both a 30 s pure tone at the neuron's CF and a wideband noise ranged from 19 to 63 s (mean 39.7±18.6) and from 9 to 31 (mean 19.4±10.5), respectively. Statistical comparison indicates that pure tone elicit longer durations of suppression ($p=0.0034$).

Effect of Non-Characteristic Sound Frequencies on the Post-Stimulus Firing

Figure 5:
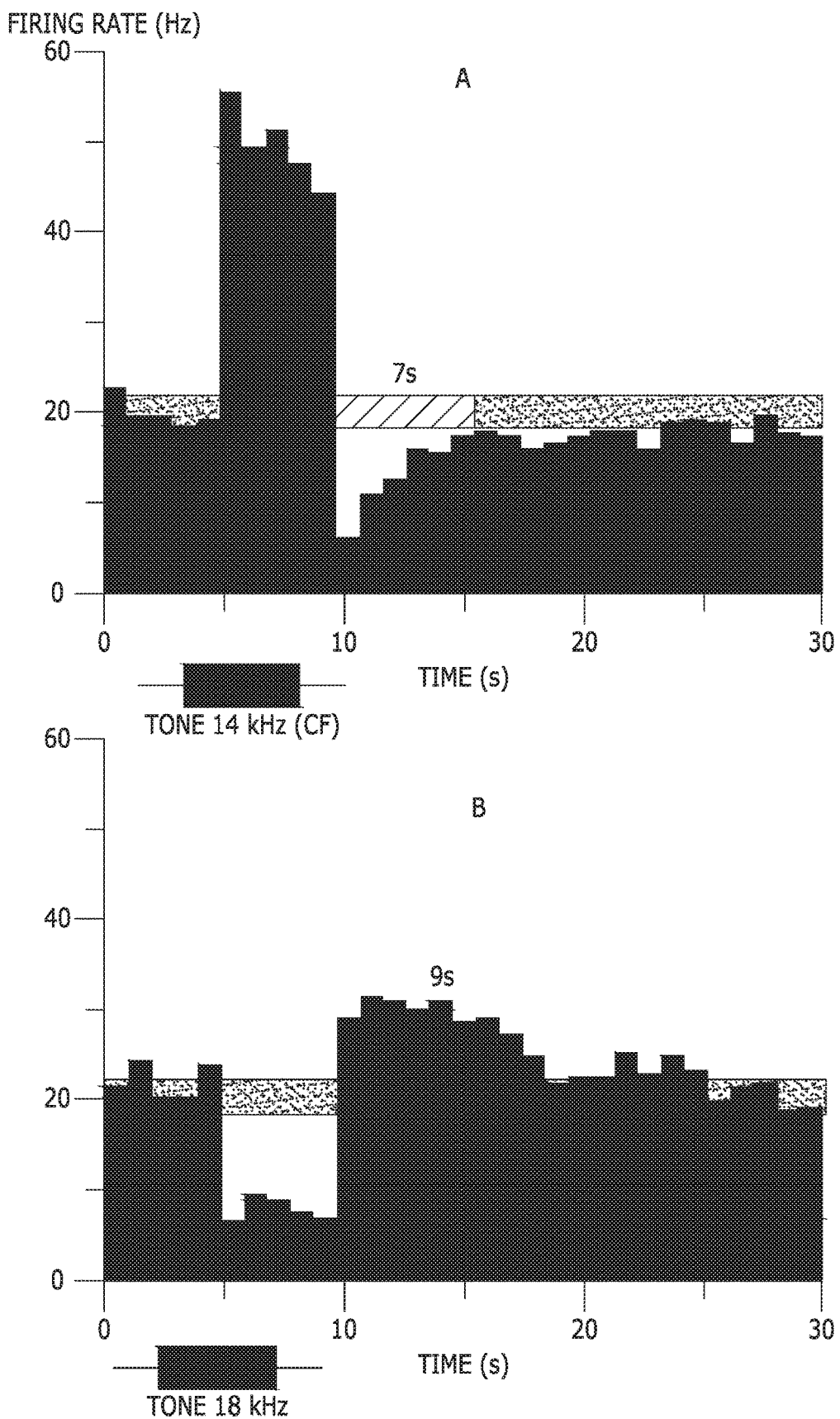
FIGS. 5A and 5B provide graphs showing that a small subset of IC neurons exhibited firing rate suppression in response to the neuron's CF, yet with facilitation to non-CFs. (A) PSTH of a single recording of an IC neuron in response to a 30 s pure tone at neuron's CF (14 kHz) presented at 75 dB SPL or 40 dB above the neuron's threshold (B) PSTH of the same neuron in response to a non-CF (18 kHz). There was 7 s duration of suppression in A and 9 s of facilitation in B.

The difference in the duration of suppression between pure tones at the neurons' CF and wideband noise suggests that the sound frequency might be critical to determine which changes in neuronal firing occur after sound presentation. To test this hypothesis, the responses of 23 IC neurons to their CF and non-CFs were studied. About half of these neurons (11/23) showed suppression to both types of stimuli, but with longer suppression durations to the neurons' CF. The average duration of suppression from 11 IC neurons to a 5 s pure tone presented at the neuron's CF and a non-CF ranged from 1.48 to 13.8 s (mean 7.06±3.38) and from 0.8 to 5.64 (mean 2.86±1.38), respectively. Statistical comparison indicates that duration of suppression to CF was statistically longer than to non-CF ($p=0.0007$). A third of these neurons ($7/23$), however, exhibited long-lasting suppression to the CF yet showed firing rate facilitation to non-CFs. A representative neuron exhibiting this type of response is shown in FIG. 5. Typical for a majority of IC neurons, this cell exhibited sustained firing during the stimulus followed by a long-lasting suppression in response to its CF. In contrast, in response to a non-CF, the firing rate was suppressed during the stimulus but was facilitated after the stimulus (FIG. 5). The remaining 5 out of 23 neurons showed suppression to the CFs and no changes in firing in response to non-CFs.

Effect of Multiple Stimulus Presentations on the Suppression

Figure 6:
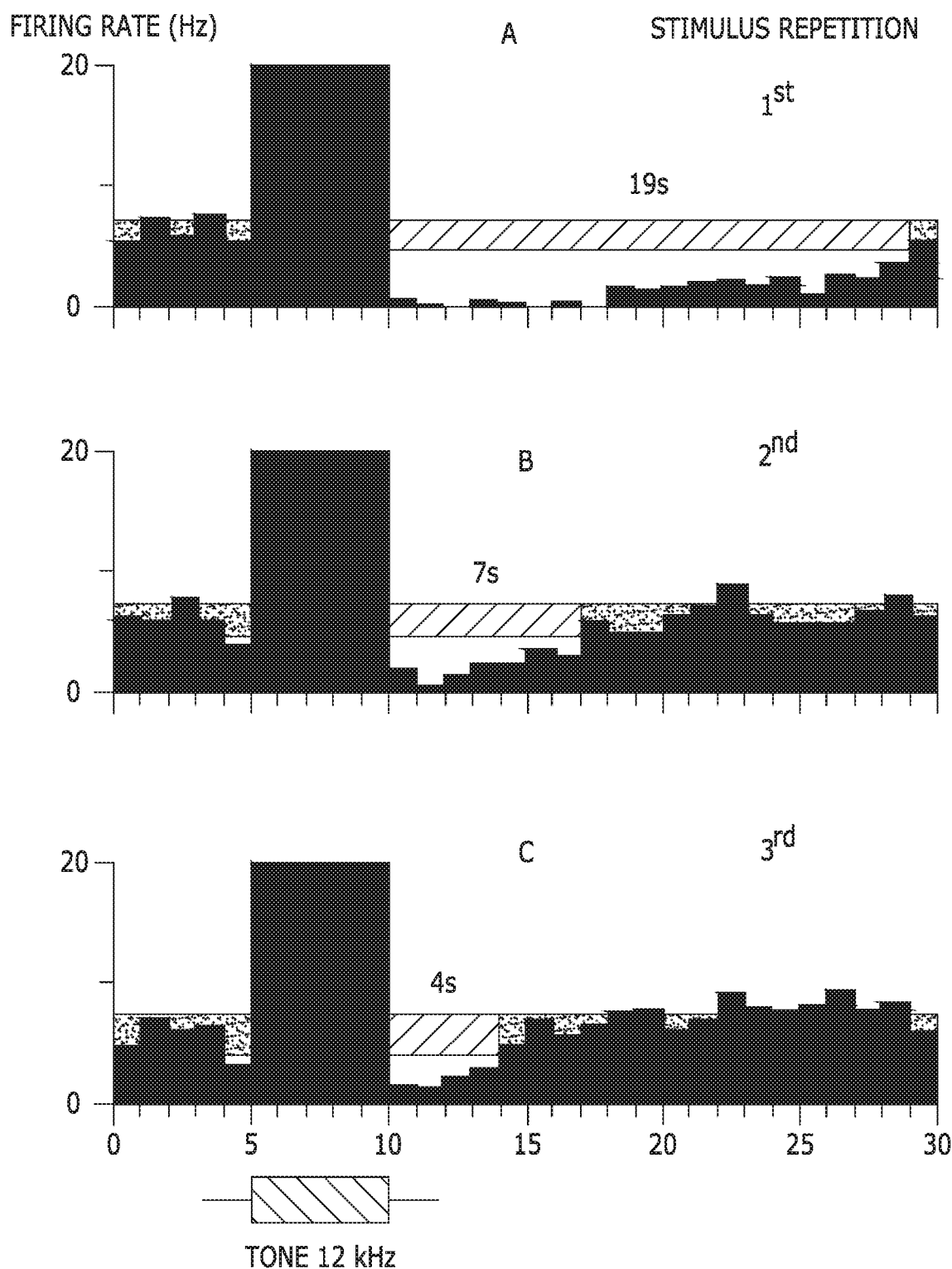
FIGS. 6A-6C provide graphs showing the duration of suppression decreased when a consecutive series of sound stimuli were presented. (A) PSTH of a single recording of an IC neuron to a 5 s pure tone at neuron's CF (12 kHz) presented at 70 dB SPL or 40 dB above the neuron's threshold. (B, C) PSTH of the same neuron in response to two more sound presentations. Note that duration of suppression decreased with each subsequent stimulus presentations (A: 19 s, B: 7 s, C: 4 s). Bin size is 1 s.

An interesting phenomenon resulting from sound stimuli presented consecutively was observed. Surprisingly about one third of IC neurons exhibiting suppression (25/69 or 36%) shortened their suppression duration with each subsequent sound presentation. A representative neuron in FIG. 6 showed suppression lasting 19 s to the first stimulus presentation (FIG. 6A). When the same sound was presented again with a short delay, the duration of suppression decreased to 7 s (FIG. 6B). The subsequent sound presentation made this suppression even shorter, about 4 s (FIG. 6C). This phenomenon was not evident when inter-stimulus intervals were extended to several minutes.

Post-Suppression Facilitation

About 40% ($28/69$) of IC neurons exhibiting suppression showed an increased firing rate compared with spontaneous firing immediately following the end of suppression. The duration of this post-suppression rebound varied among neurons, ranging from 5 to 42 seconds when a 30 s sound stimulus was presented. A representative neuron in FIG. 7 elicited a 24 s suppression in response to a 30 s pure tone presented at the neuron's CF. By the end of this suppression the firing rate was significantly increased for about 33 s compared to the pre-stimulus level.

Long-Lasting Suppression in Auditory Cortex Neurons

The inventor studied sound-evoked suppression in 39 spontaneous firing neurons in the auditory cortex of 12 awake mice. Similar to the IC, the majority of AC neurons ($24/39$ or 61%) exhibited long-lasting suppression after a sound stimulus was presented. In contrast to IC neurons, which predominantly exhibited sustained responses during stimulus duration, more than half of AC neurons ($22/39$ or 56%) responded to the beginning of the sound stimulus. During the remaining time of the stimulus their spontaneous activity was largely suppressed. A representative neuron in FIG. 8 had a spontaneous firing rate of 4.3 Hz before the stimulus. During and after a 30 s wideband noise stimulus, the firing rate in this neuron was greatly suppressed. The suppression after stimulus offset lasted 89 s until firing returned to the pre-stimulus level.

The basic features of the suppression in the IC and AC were very similar. AC neurons also exhibited longer suppression to pure tones compared to wideband noise stimuli ($7/8$ neurons tested or 88%) and showed a progressive reduction in the suppression duration ($4/14$ neurons tested or 29%) when sound stimuli were presented consecutively. Similar to the IC, AC neurons often ($9/39$ or 23%) showed facilitation of neuronal firing immediately after the end of suppression.

Suppression of Spontaneous Firing in Mice with Behavioral Evidence of Tinnitus

The data presented above were collected in normal, tinnitus-free animals. To determine whether animals with tinnitus also exhibit long-lasting suppression, a group of mice with behavioral evidence of tinnitus was studied. Ten animals were exposed unilaterally for one hour to a 116 dB SPL one octave narrow-band noise centered at 12.5 kHz, a common method in the field of tinnitus research used to induce tinnitus. Galazyuk A V, Hebert S, Front Neurol 6:88 (2015). Three months following exposure, behavioral testing identified evidence of tinnitus in 4 out 10 exposed animals, which is a typical outcome for a given sound exposure. In agreement with numerous previous reports, the average spontaneous firing rate of IC neurons in tinnitus mice was much higher compared to controls. Longenecker R J, Galazyuk A V, J Assoc Res Otolaryngol 12:647-658 (2011). The firing rates of IC neurons in tinnitus positive mice ranged from 0.8 to 98 sp/s, with a mean of 27.71 sp/s, which was about five times higher than that of controls ($p<0.00001$). Similar to controls, about half of IC neurons ($23/54$ or 42%) in the mice with behavioral evidence of tinnitus also showed long-lasting suppression (FIG. 9A). The duration of this suppression in tinnitus positive animals did not significantly differ from control animals ($p=0.08$) (FIG. 9B).

DISCUSSION

The primary goal of this work was to identify the cellular mechanism of RI, a behavioral phenomenon known for more than 100 years. Using sound stimuli analogous to those used for triggering RI in humans, we found that many auditory neurons in mice exhibit long-lasting suppression of their spontaneous neuronal firing following sound presentation. There are a number of striking similarities between the basic parameters of this suppression and RI. Since elevated spontaneous firing (hyperactivity) in auditory neurons has been linked to tinnitus, suppression of this hyperactivity with sound may explain a temporary relief from tinnitus during the RI. This study presents the first direct demonstration of a link between a cellular mechanism of sound processing in auditory neurons and the behavioral phenomenon of RI. The similarities between the RI and suppression individually as well as the possible significance of this suppression in sound processing are discussed below.

Similarities Between RI and Suppression

Duration of RI and Suppression Increase with Sound Duration

Although it is not linear, the duration of RI has been shown to increase with sound duration. Tyler R S, Conrad-Armes D, J Speech Hear Res 27:106-111 (1984). Audiologists typically test tinnitus patients for RI by using 30 s or 1 min sounds. In response to these stimuli the majority of patients report RI lasting about one minute on average. Similarly the duration of the suppression in the auditory neurons in the present study also increased with sound duration and lasted on average 40 s in response to a 30 s sound stimulus (FIGS. 2 and 3).

Effect of Stimulus Spectrum on Suppression Duration

Current literature concerning RI outlines some disagreement among studies on the differential effectiveness of pure tones vs noise for induction of RI. However, a majority of studies report that pure tones are more effective at inducing RI compared to wideband or even narrowband noise stimuli. Sockalingam et al., Audiological Medicine 5:92-102 (2007). Both the depth and duration of RI are increased when the trigger sound matches the frequency range of the patient's tinnitus. Roberts et al., J Assoc Res Otolaryngol 9:417-435 (2008). The inventor observed a similar trend in both IC and AC: pure tones were more likely to trigger longer suppression of neuronal firing in auditory neurons compared to wideband noise (FIG. 4).

An unusual phenomenon was observed in 30% of auditory neurons when their responses were tested to CF and non-CFs. These neurons showed a typical suppression in response to neurons' CF, yet exhibited long-lasting facilitation to non-CFs. A long-lasting increase in tinnitus loudness has also been reported by some tinnitus patients during RI induction. Lipman R I, Lipman S P, Otolaryngol Head Neck Surg 136:763-768 (2008). The data strongly suggest that this unusual phenomenon might occur as a result of a mismatch between the frequencies of the sound stimulus and a patients' tinnitus, especially in the case of tonal tinnitus. For example, a patient with 6 kHz tinnitus was presented a 10 kHz sound to induce RI, many hyperactive neurons having a CF of 6 kHz (tinnitus frequency) would be stimulated with a non-CF (10 kHz). Based on the results some of auditory neurons in the tinnitus frequency region would show firing rate facilitation instead of suppression which may be perceived as a temporary increase in tinnitus loudness.

The Effect of Multiple Stimulus Presentations on the Suppression

The inventor has demonstrated that some auditory neurons exhibited a reduction in the duration and "depth" of the suppression of spontaneous firing rates when stimuli were presented with relatively short inter-stimulus intervals (FIG. 5). Interestingly, this effect resulting from repeated RI inductions has not been often reported in human RI studies. Therefore it is possible that this phenomenon has not been widely observed and described. However, a recent intracranial mapping study on a single human patient did corroborate with the results. Sedley et al., Curr Biol 25:1208-1214 (2015). When RI was induced repeatedly with relatively short inter-stimulus intervals the efficacy of RI induction was largely reduced.

Post-Suppression Facilitation

Figure 7:
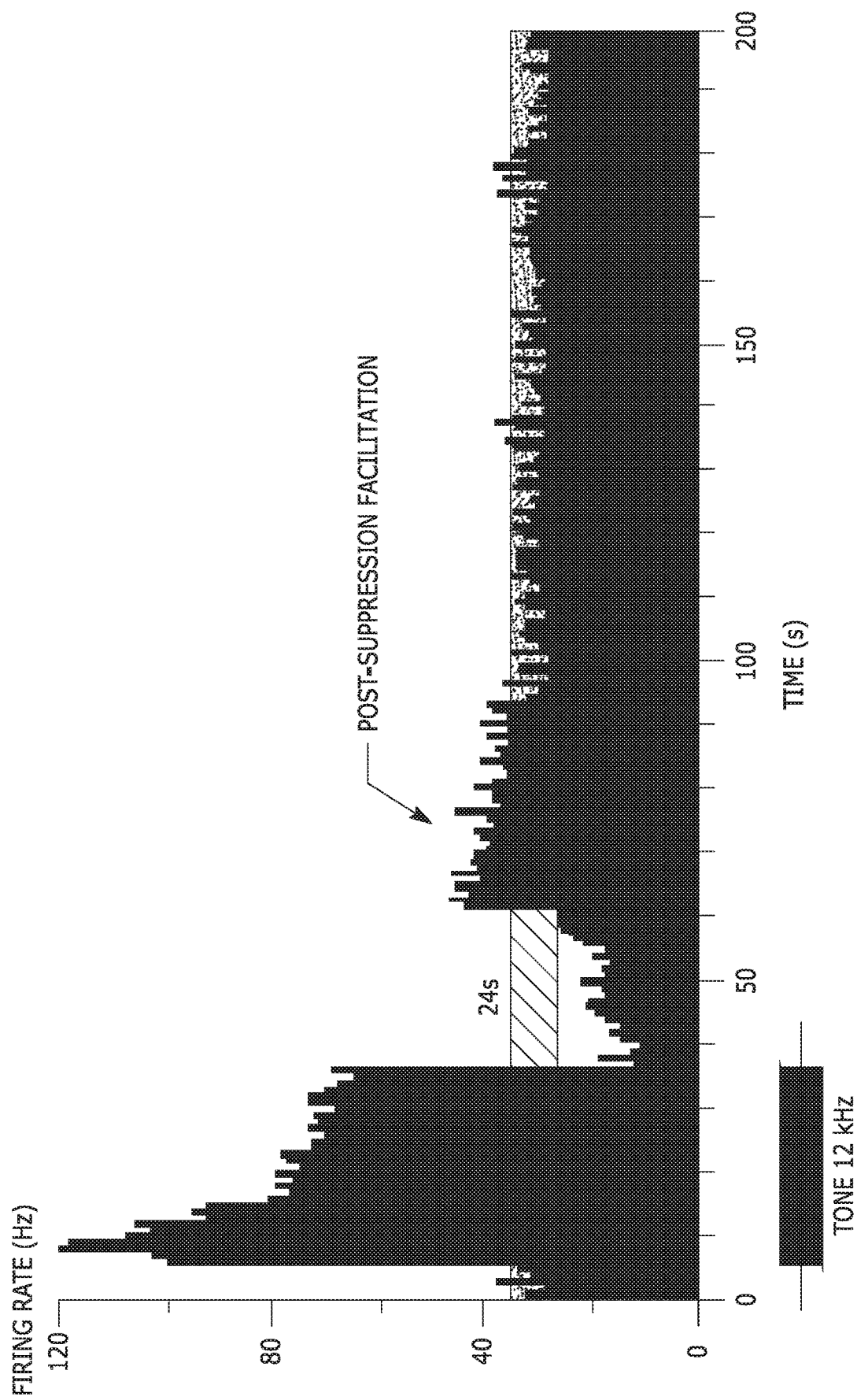
FIG. 7 provides a graph showing the facilitation of spontaneous firing in an IC neuron following sound-evoked suppression. PSTH of a single recording of an IC neuron in response to a 30 s pure tone presented at the neuron's CF (12 kHz) at 60 dB SPL or 40 dB above the neuron's response threshold. Black arrow indicates the facilitation.
Figure 8:
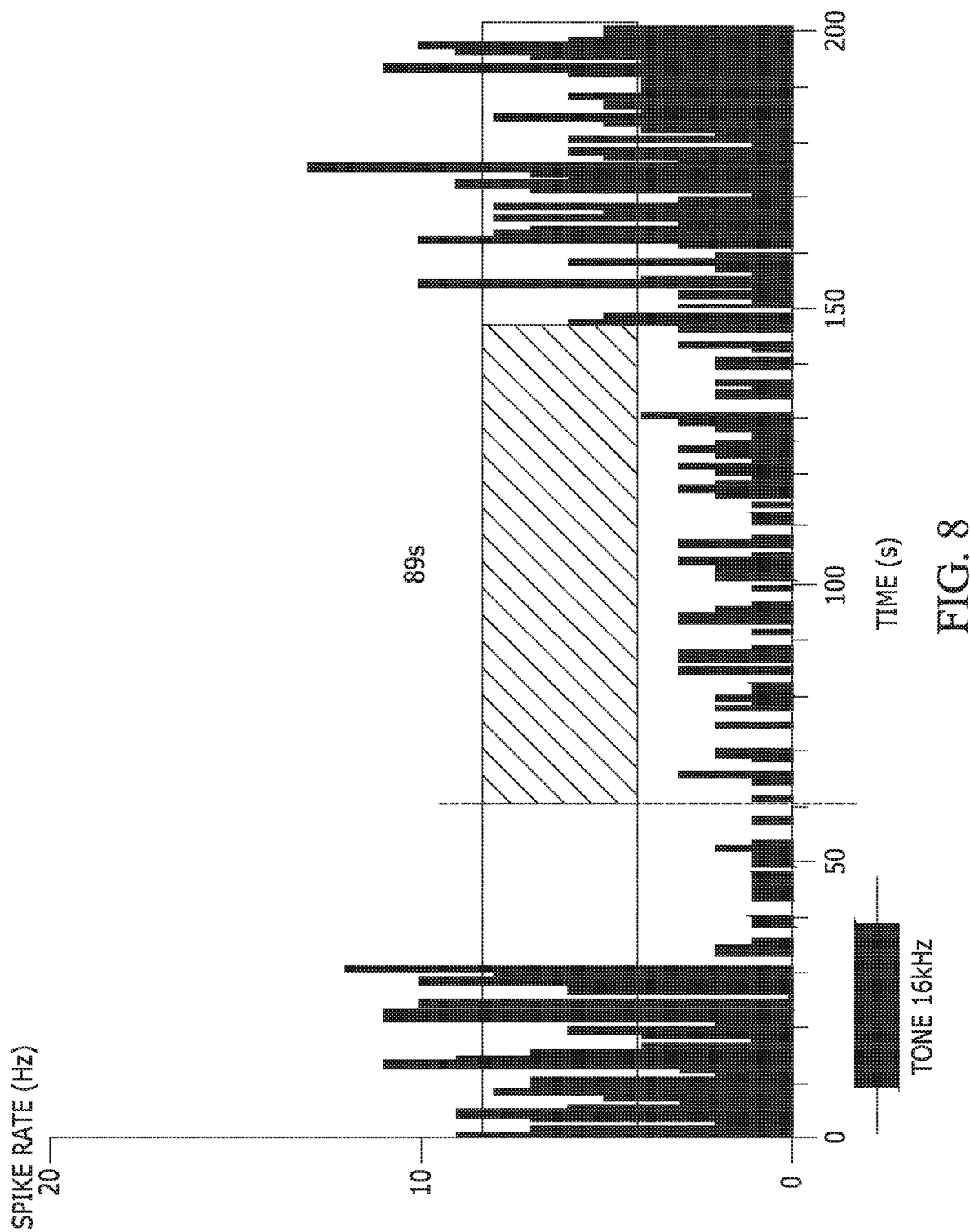
FIG. 8 provides a graph showing the facilitation of spontaneous firing in an IC neuron following sound-evoked suppression. PSTH of a single recording of an IC neuron in response to a pure tone 30 s duration presented at the neuron's CF (16 kHz) at the level of 65 dB SPL or 40 dB above the neuron's response threshold. The vertical dashed line indicates the time of stimulus offset.
Figure 9:
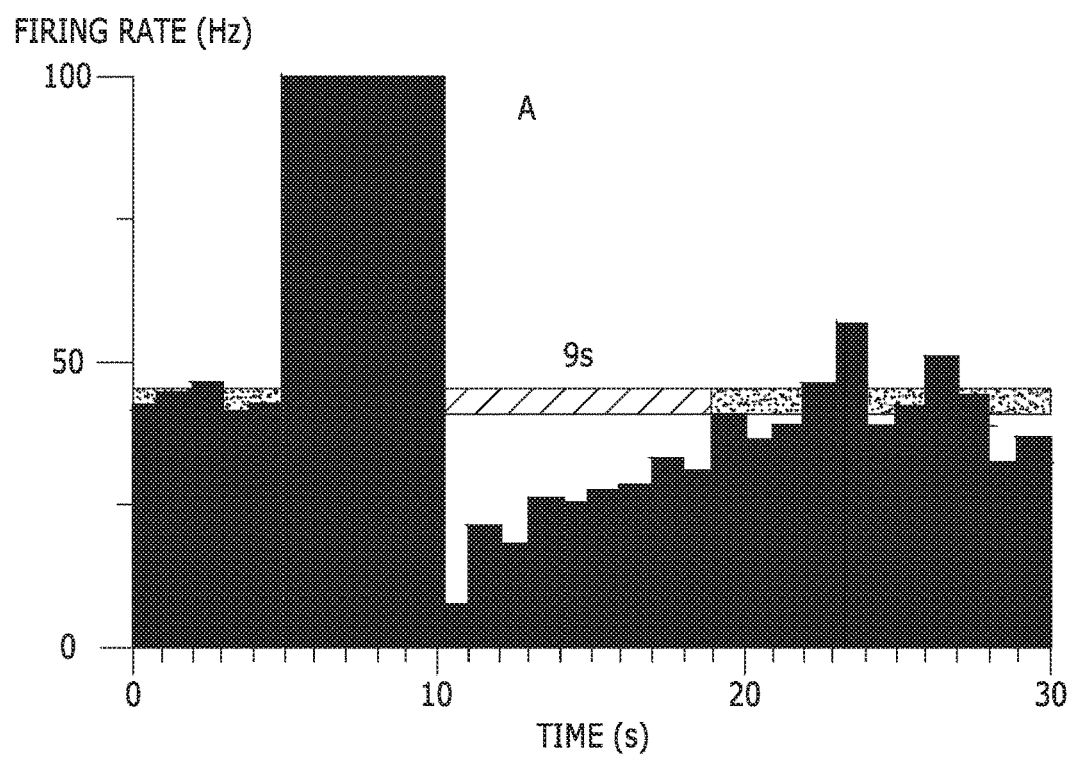
FIGS. 9A and 9B provide graphs showing the suppression of spontaneous firing in IC neurons of tinnitus positive and naïve mice is similar. (A) PSTH of a single recording of an IC neuron in a tinnitus positive mouse to a 5 s pure tone presented at the neuron's CF (25 kHz) at 70 dB SPL or 40 dB above the neuron's response threshold. (B) Comparison of the duration of suppression to 5 s sound stimuli presented at neurons' CF in IC neurons of the control and tinnitus positive mice.
Figure 9:
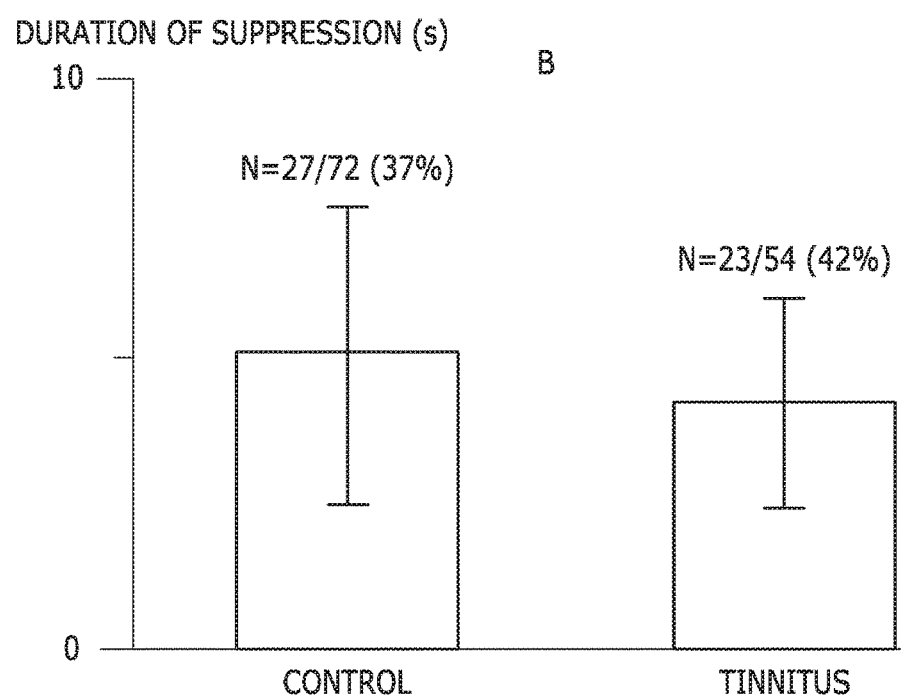

The ~40% of auditory neurons in our study that exhibited suppression also showed a momentary increase in firing rate immediately following cessation of suppression (FIG. 7). Further research is needed to determine whether post RI facilitation is also a typical phenomenon during RI induction in humans.

What does Neural Suppression Tell Us about the Mechanisms of RI and Tinnitus?

The most surprising cumulative finding from the present study is that suppression is likely a universal sound processing phenomenon observed across species and appears to be tinnitus independent. The inventor found no differences in the main features of the suppression in either tinnitus positive or negative mice. Although it has not been studied systematically in relation to RI, stimulus-induced suppression has been observed at almost all levels of the central auditory system and in different mammalian systems. Smith R L, J Neurophysiol 40:1098-1111 (1977). Therefore it would be logical to expect that this phenomenon should also be present in humans. This notion leads to the dubious question of why is it that only people with tinnitus experience RI. In an attempt to answer this question, it is useful to consider the theory that the tinnitus percept results from hyperactive or highly spontaneously active neurons. Based on this theory, elevated spontaneous activity arises in the central auditory system in response to cochlear damage. Roberts et al., J Neurosci 30:14972-14979 (2010). Apparently the brain perceives this hyperactivity as a phantom sound or tinnitus. When a tinnitus patient experiences RI after a sound stimulus, this sound stimulus may be lowering the spontaneous rate of his/her neurons for a brief period of time. Alternatively, normal individuals would not experience RI because their spontaneous activity levels in the auditory system would be low enough to remain below the threshold of sensation. For these individuals, suppression of this activity with an external sound would be unnoticeable. As tinnitus is considered to be tightly linked to elevated spontaneous activity, and we have shown that the characteristics of RI and neural response suppression are closely matched, it is likely that suppression of elevated spontaneous activity explains the suppression of tinnitus seen in ~80% of patients during RI.

Suppression and Sound Processing

The present and previous research suggest that post stimulus suppression of spontaneous firing is a typical sound processing phenomenon. Real-world acoustic signals, including human speech, rarely occur in isolation and usually comprise a sequence of sound elements. If an auditory neuron exhibits suppression, the entire sequence will be processed by this neurons without or with reduced spontaneous firing. Therefore, suppression of spontaneous firing may serve as a mechanism of enhancing signal-to-noise ratio during signal processing. However, there is some indirect evidence suggesting that the signal-to-noise ratio might not be the only advantage of the suppression. It has been demonstrated that response selectivity of auditory neurons to sound level, frequency, and duration, can be greatly enhanced if sound stimuli for assessing such selectivity are presented with high repetition rates. If the stimulation rate is high, the stimuli are likely to be analyzed by auditory neurons within the time of suppression.

Example 2: A mGluR Targeted Drug Controls Firing Activity in IC Neurons

Background

Figure 10:
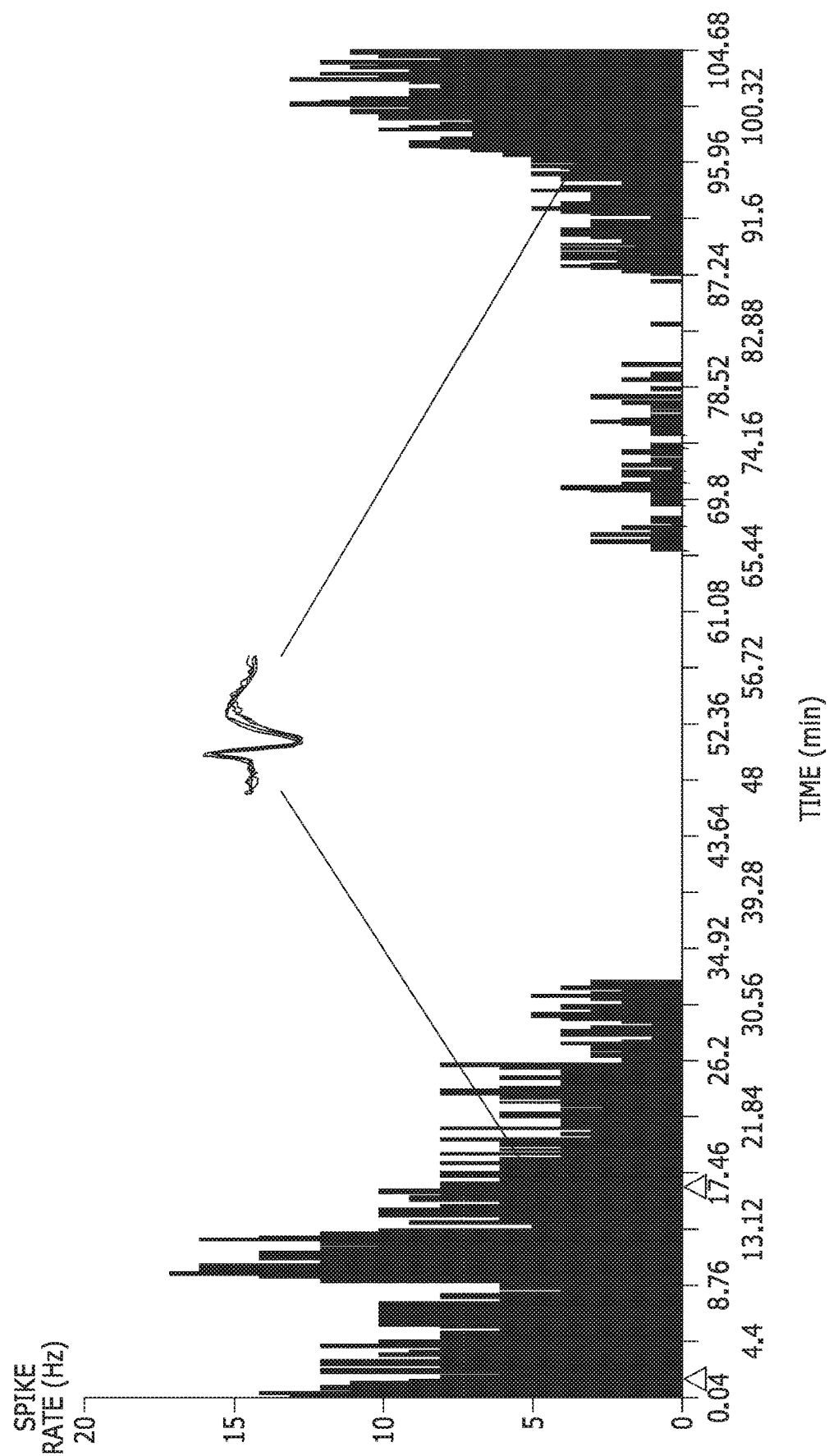
FIG. 10 provides a graph showing that a group II mGluR agonist suppresses spontaneous activity in IC neurons. Spike waveforms collected at the beginning and at the end of recording session (center top) indicate that the same cell was recorded throughout the session. Time of drug administration is indicated by black arrows. Population data from 5 IC neurons are shown on the top right corner.

Sound exposure often results in hyperactivity throughout the auditory system. The current consensus is that it plays a role for etiology of tinnitus. Theoretically, pharmacological agents that reduce hyperactivity or elevated spontaneous activity in auditory neurons could suppress tinnitus. The work carried out in Example I suggested that metabotropic glutamate receptors (mGluRs) play a role in controlling neuronal activity in the auditory system (FIG. 10, 13, 15). Furthermore the results demonstrate that effects of activation group II mGluRs has differential effects on spontaneous and sound evoked activity in auditory neurons. Systemic activation of group II mGluRs with group specific agonist LY354740 did not change or slightly increased sound evoked activity (FIG. 13) whereas dramatically suppressed spontaneous activity in these neurons (FIG. 10, 15). Therefore the inventor investigated whether systemic injection of type II mGluR agonists can alter firing of auditory neurons. If so, it would open an opportunity to develop a drug which could suppress tinnitus in humans.

Methods

Adult CBA/CaJ mice were used for the study. Neuronal firing in the inferior colliculus of awake mice was recorded extracellularly before, during, and after systemic injection of group II mGluR agonist LY354740. Injection was performed remotely via an intravenous catheter inserted into the tail vein. Spontaneous firing rates of IC neurons were measured and compared before, during, and after of drug injection. To test whether this drug is affecting general sound processing in the auditory system of mice, the acoustic startle reflex and gap detection performance were also assessed.

The animals used were CBA/CaJ male mice, 8 months to 1.5 years old. Extracellular recording was carried out using Quartz micropipettes filled with 1M potassium acetate solution, 10-20 M ohms. Local field potential (LFP) was evaluated using a chronically implanted 4 channel multi-electrode array chronically implanted into IC in a freely moving animal via wireless recording system. For drug administration, the Group II mGluR agonist was administered via intravenous (3.5 mg/kg) or intraperitoneal (5 mg/kg) injections while recording neural activity. To evaluate startle input/output function, startle intensities were randomized within the range from 70 dB to 120 dB SPL. Startle was a broad band noise 20 ms duration. Inter-trial intervals were pseudo randomized between 15 and 25 sec. For gap detection, two trials were carried out. Trial I—The acoustic startle (110 dB SPL, 20 ms duration, wideband noise) imbedded in continuous background noise (65 dB SPL, third octave, centered at 10, 12.5, 16, 20, 25, and 31.5 kHz). Trial II—Trial I paired with a 20 ms gap embedded into background noise and presented 100 ms before the startle. Inter-trial intervals were pseudo randomized between 10 and 17 sec.

Results

Figure 14:
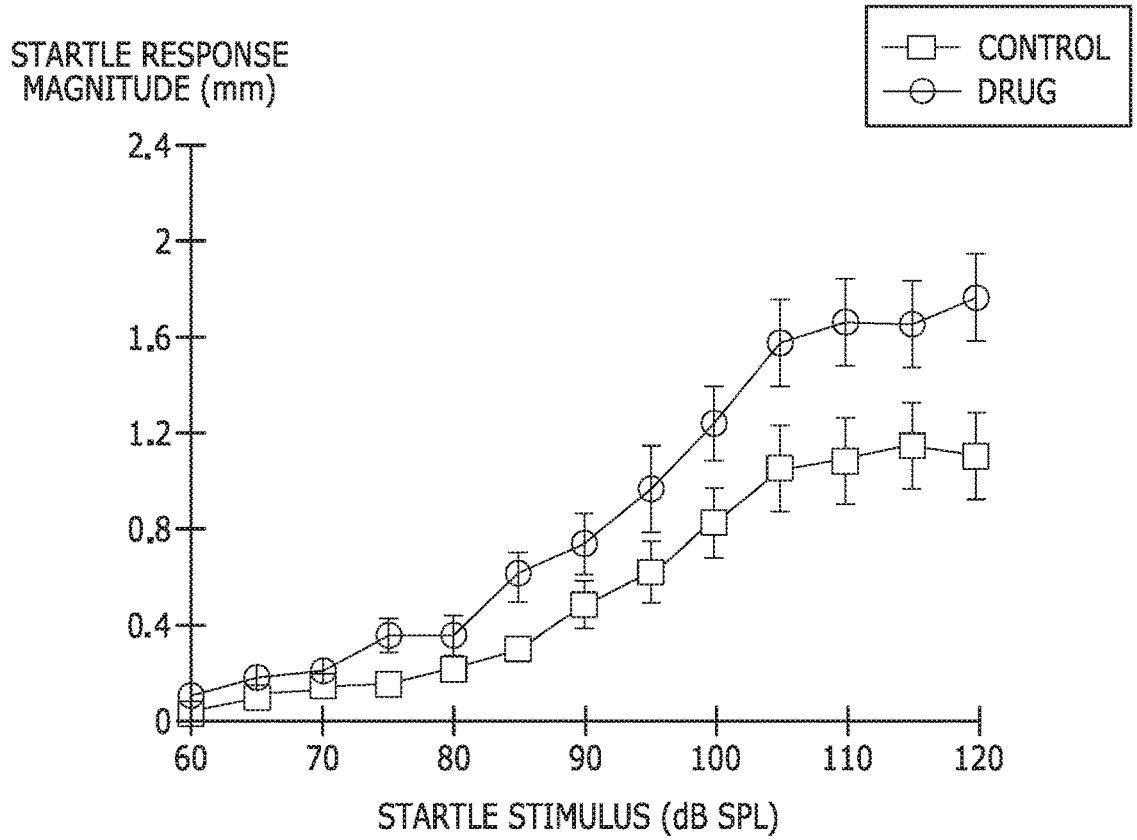
Figure 14:
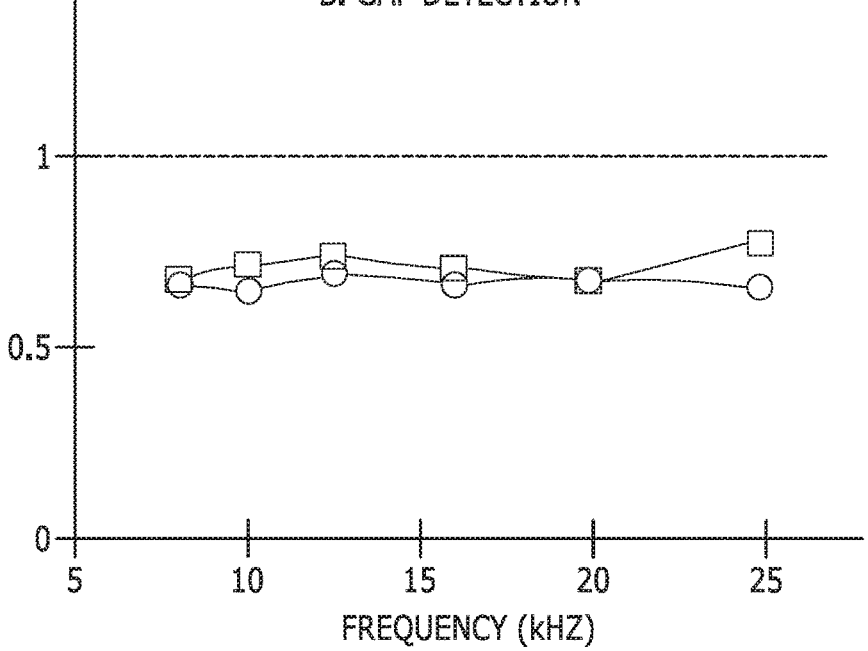

The LY354740 injected IV had a quick and dramatic effect on the spontaneous activity in IC neurons. Several seconds after injection the vast majority of IC neurons exhibited near complete suppression of their spontaneous activity lasting several tens of minutes. The magnitude of startle responses was increased at least 20% in 6 out of 7 mice tested (FIG. 14, A). The gap detection performance, however, was not affected by the drug (FIG. 14, B).

Figure 11:
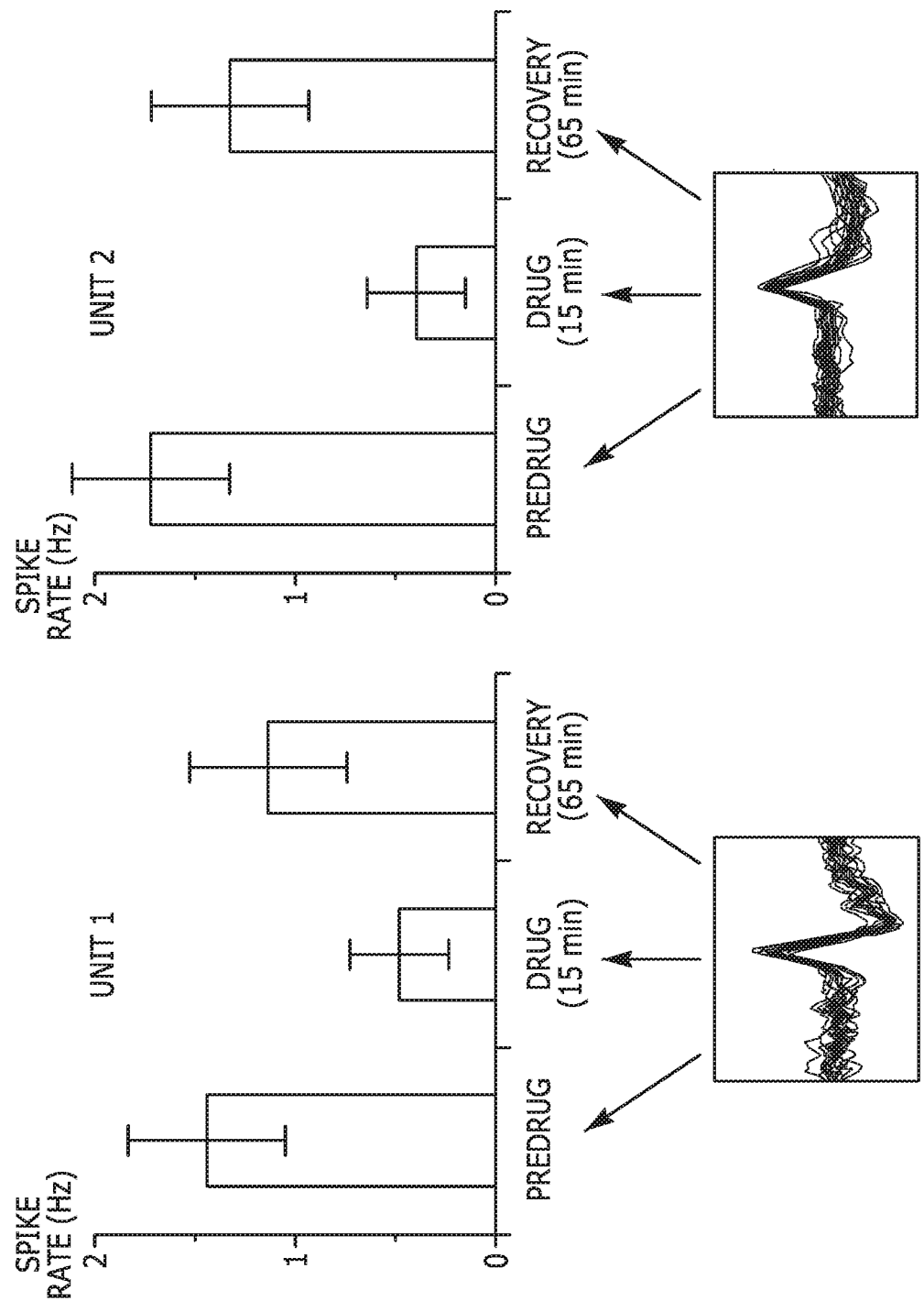
FIG. 11 provides graphs and images showing the suppression of spontaneous activity in the amygdale. Two representative neurons from amygdala which responded to sound and exhibited suppression of their spontaneous activity after the drug administration. The similarity of the waveforms collected before, during and after drug administration for these two neurons (shown below) indicate that the same neuron was recorded throughout the recording sessions.

FIG. 11 illustrates the drug effect on spontaneous activity in the amygdala (limbic system, responsible for emotions). Hyperactivity in the limbic system has been observed in tinnitus animal models and humans and is suggested to be responsible for tinnitus-related distress. Two representative neurons from amygdale exhibit suppression of their spontaneous activity after the drug administration. The similarity of the waveforms collected before, during and after drug administration for these two neurons indicate that the same neuron was recorded throughout the recording sessions.

Figure 12:
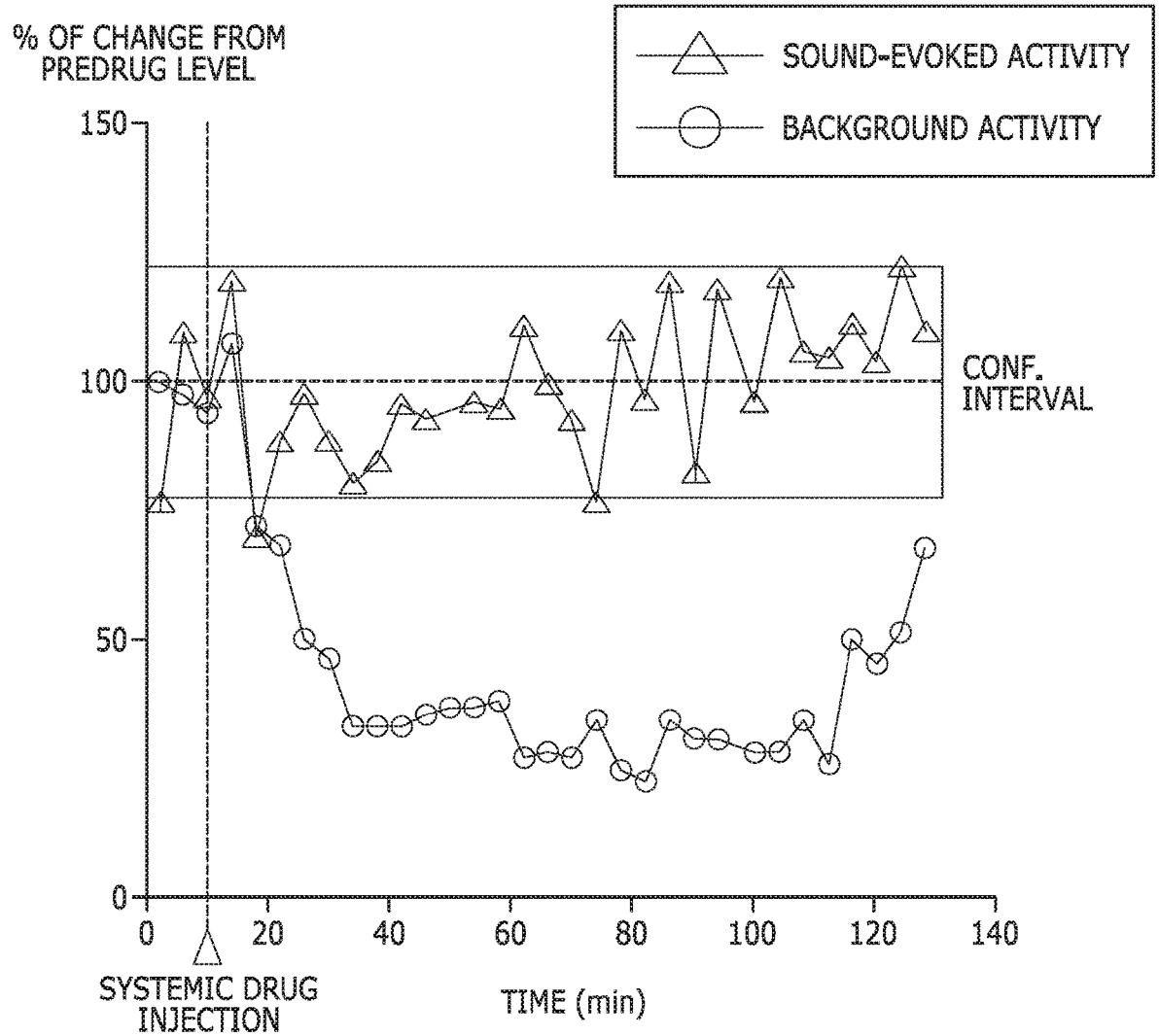
FIG. 12 provides a graph showing the selective effect of LY354740 (Eglumegad) on background or spontaneous firing activity in an IC neuron. About 5 min after systemic drug administration (indicated by a dashed vertical red line) background firing in this neuron was suppressed (black circles), whereas sound-evoked firing was unaffected (open circles). Note, that about 2 hours later the rate of background activity was almost recovered to the pre-drug level.

FIG. 12 illustrates that the drug effect on neuronal firing in the auditory midbrain is selective by suppressing spontaneous activity whereas sound evoked activity remains unaffected. Such selective drug effect strongly suggest that people who will be taking this drug for tinnitus treatment will unlikely experience their hearing to be compromised by the drug.

Figure 13:
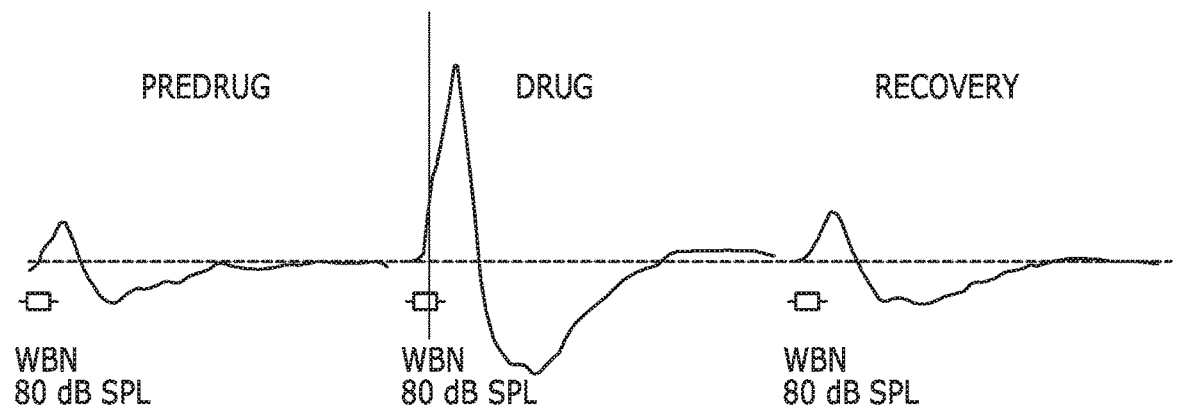
FIG. 13 provides graphs showing that a group II mGluR agonist enhances of sound evoked activity in the IC. Local field potentials (LFPs) recorded in the IC of awake mice in response to 30 ms wideband noise (1-100 kHz, 80 dB SPL) recorded before, 30 min and 90 min after drug administration. LFPs shown here were generated based on 130 repetitions. SEMs are shown by grey FIGS. 14A and 14B provide graphs showing that a group II mGluR agonist enhances startle response, but does not alter gap detection performance. A. Startle input-output functions (averaged across 7 mice) before (control) and 30 min after drug administration. B. Gap detection performance in the same 7 mice shown in A before and after 30 min after drug administration.

FIG. 13 illustrates the drug effect on sound evoked activity in the inferior colliculus (auditory midbrain). (I am not sure whether the following sentence belong to here or it should be moved to the conclusion) After systemic drug administration the responses to sounds were slightly enhanced, whereas the same drug suppressed spontaneous activity of inferior colliculus (FIG. 10, 15) or amygdale neurons (FIG. 11).

CONCLUSION

LY354740 has the potential to be used as a drug to control tinnitus. Future studies should determine its effect on sound-evoked activity in auditory neurons as well as whether it can suppress behavioral signs of tinnitus in tinnitus animal models.

To understand the presentation of tinnitus in animals, we developed a preclinical tinnitus mouse model to show how the auditory system and brain perceive sound and sound linked to tinnitus.

Spontaneous Activity and Tinnitus

Figure 15A:
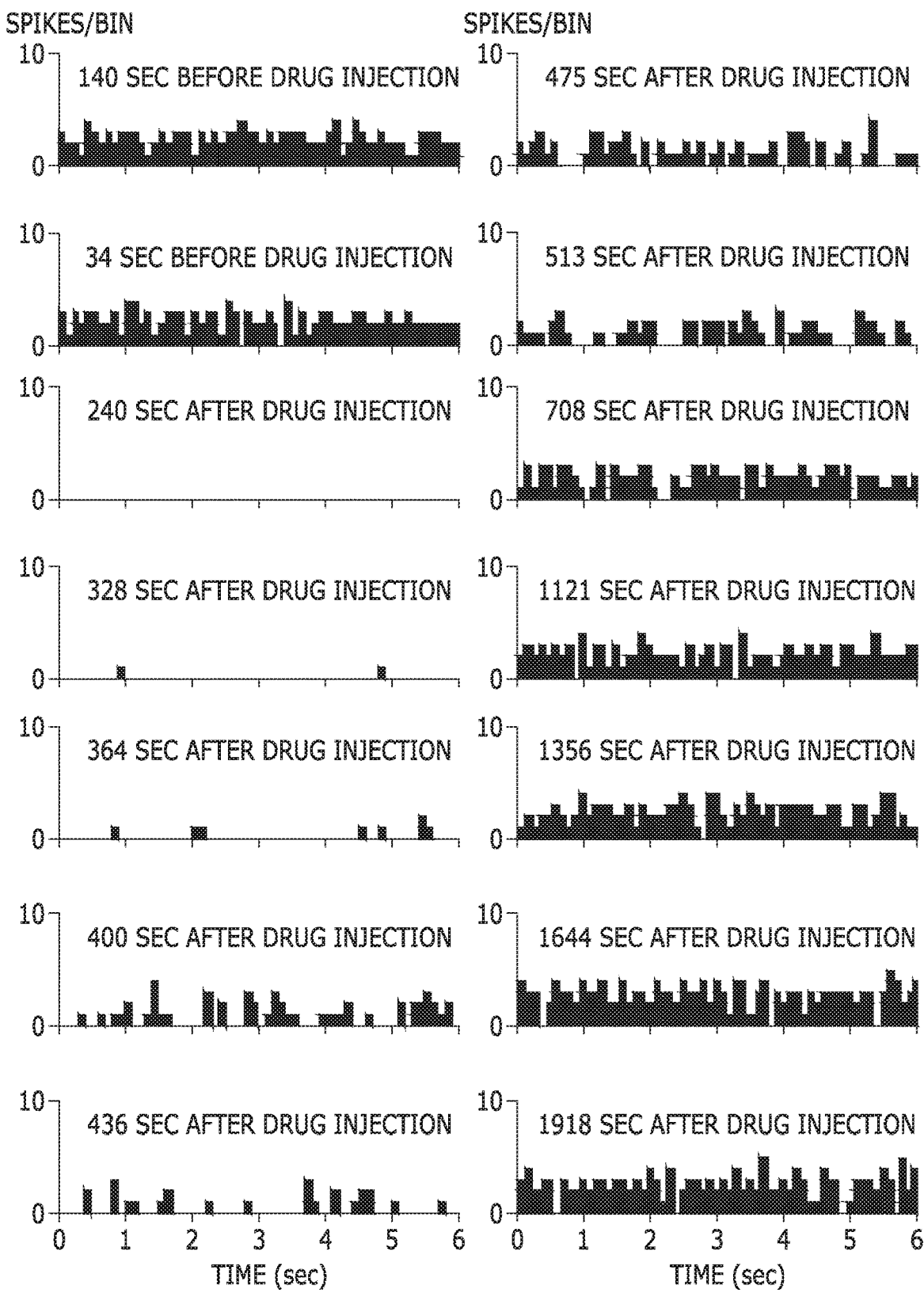
FIG. 15 provides graphs showing the suppressive effect of systemic administration of group II mGluR agonist LY354740 on spontaneous firing of an auditory neuron in the brain of the mouse.
Figure 15B:
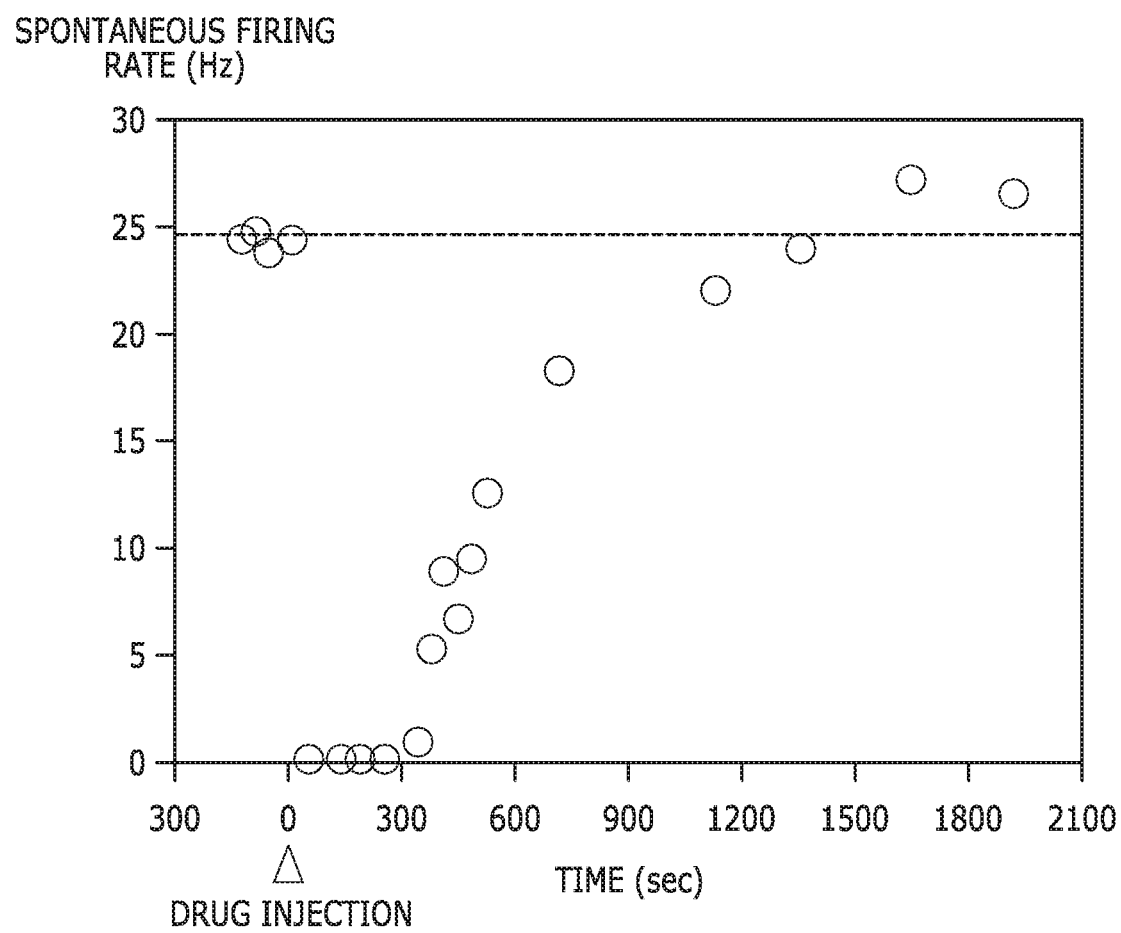

An elevated spontaneous activity in the auditory system in the brain has been linked to tinnitus. Suppression of this activity should suppress tinnitus sensation. This is demonstrated by FIG. 15, which shows the suppressive effect of systemic administration of group II mGluR agonist LY354740 on spontaneous firing of an auditory neuron in the brain of the mouse.

Figure 16:
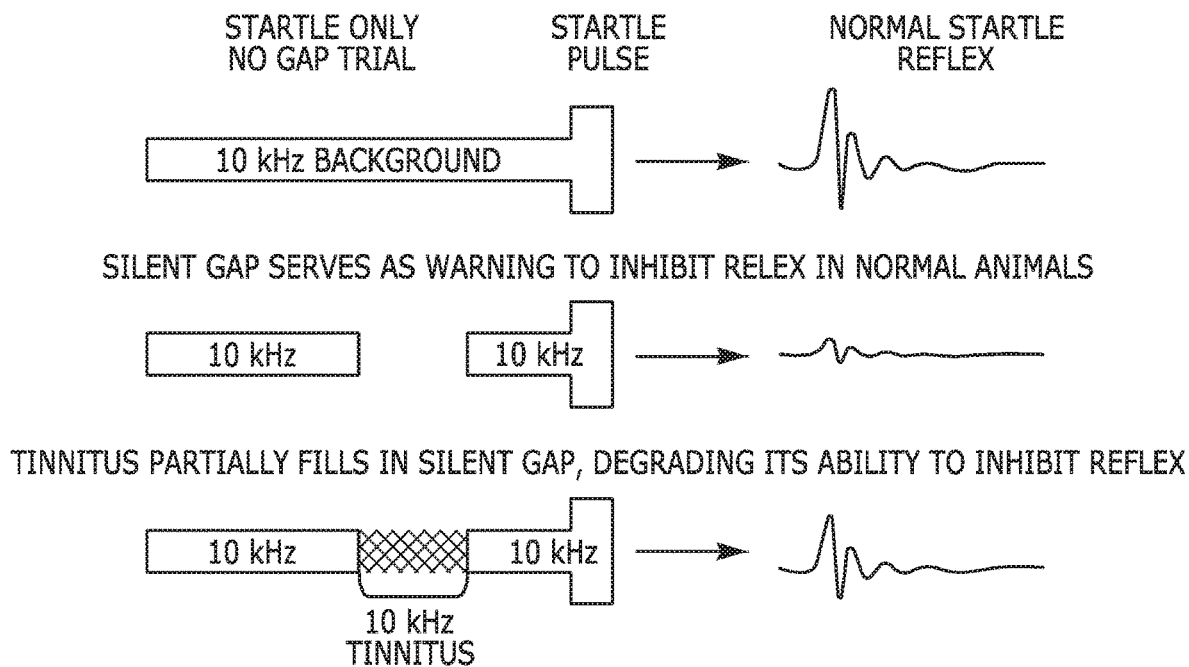
FIG. 16 provides a schematic representation of the behavioral model utilizing gap-induced suppression of the acoustic startle reflex for tinnitus assessment in laboratory animals.

Once the preclinical model was validated, a test to determine reflexes was demonstrated. The presence of tinnitus in each mouse is assessed by pre-pulse inhibition of the acoustic startle reflex using the procedure developed by Turner et al. Turner et al., Behav Neurosci 120:188-195 (2006). Animals experiencing tinnitus are expected to perform poorly in this test because their tinnitus fills the gap of silence that precedes the startle-eliciting noise burst (FIG. 16). A statistically significant reduction in the pre-pulse inhibition in experimental versus control mice was used as an indicator of tinnitus. A commercially available hardware/software system designed specifically for this purpose was used to assess tinnitus in mice (Kinder Scientific, LLC). This system is capable of computer-controlled measurements of prepulse inhibition of the startle reflex in several mice simultaneously. One-way analyses of variances (ANOVAs) was used for statistical data analysis. The inventor measured the ratio of the startle response amplitude when preceded by a gap of silence over the startle response amplitude without preceded gap. The ratio of 1 means no gap detection (or an indication of tinnitus), whereas the ration of 0 means very good gap detection (no tinnitus).

Figure 17:
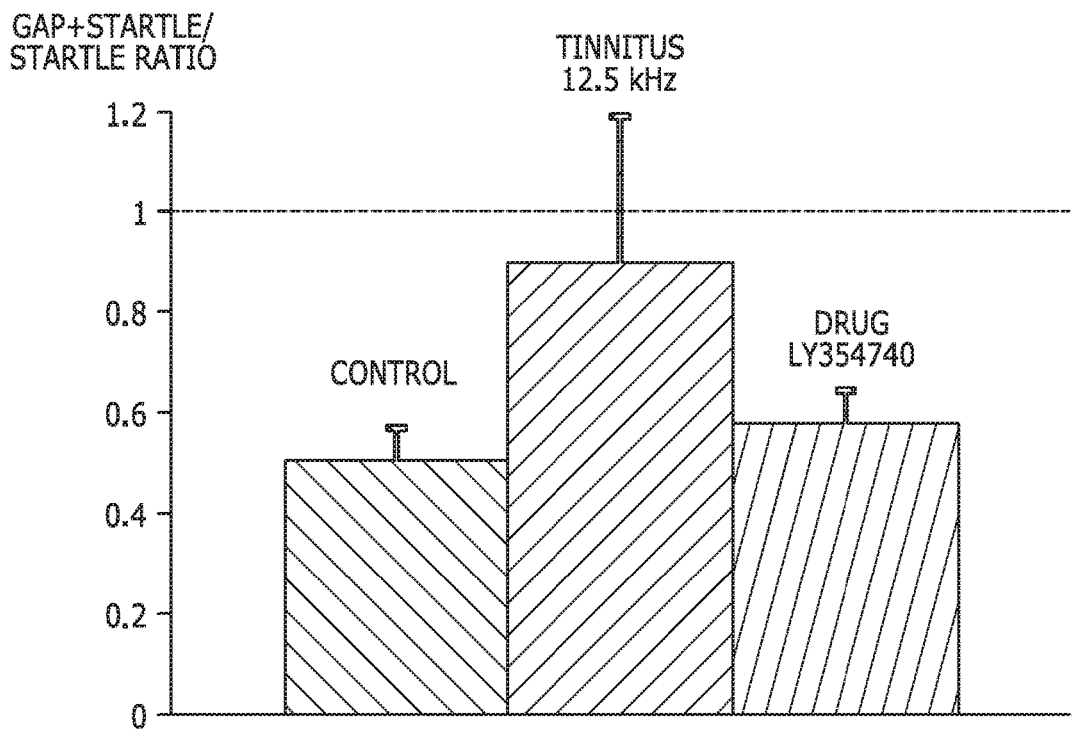
FIG. 17 provides a graph showing the enhancement of gap detection performance in a mouse after systemic injection of LY354740. Poor gap detection has been linked to tinnitus. If so, improvement of gap detection in this mouse to the control level suggests that tinnitus was eliminated by the drug.

FIG. 17 shows Enhancement of gap detection performance in a mouse after systemic injection of LY354740. Poor gap detection has been linked to tinnitus (see FIG. 15 for explanation). If so, improvement of gap detection in this mouse to the control level suggests that tinnitus was eliminated by the drug. The inventor demonstrated that the addition of LYS354740 was shown to positively reduce the tinnitus with this drug.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of temporarily suppressing tinnitus in a subject, comprising administering a therapeutically effective amount of a group II metabotropic glutamate receptor (mGluR) agonist to the subject.

2. The method of claim 1, wherein the group II mGluR agonist is selected from the group consisting of (1S,3R)-ACPD, cis-ACPD, (±)-trans-ACPD, (2R,4R)-APDC, (S)-3-Carboxy-4-hydroxyphenylglycine, (S)-4-Carboxy-3-hydroxyphenylglycine, (S)-4-Carboxyphenyglycine, L-CCG-I, DCG IV, LY354740, LY379268, (±)-LY395756, MAP4, NPEC-caged-LY379268, and spaglumic acid, and pharmaceutically acceptable salts thereof.

3. The method of claim 1, wherein the group II mGluR agonist is LY354740 or an LY354740 prodrug, or a pharmaceutically acceptable salt thereof.

4. The method of claim 3, wherein the subject is human, and a dose of LY354740 from about 100 to 200 mg/day is administered.

5. The method of claim 1, wherein the group II mGluR agonist is administered systemically.

6. The method of claim 1, wherein the group II mGluR agonist is administered with a pharmaceutically acceptable carrier.

7. The method of claim 1, wherein the tinnitus is subjective tinnitus.

8. The method of claim 1, wherein administration of group II mGluR agonist provides suppression of tinnitus for about 5 to about 25 minutes following administration.

9. A method of screening a subject having tinnitus for temporary suppression of tinnitus with a group II metabotropic glutamate receptor (mGluR) agonist, comprising testing the use of residual inhibition to suppress tinnitus in the subject, wherein suppression of tinnitus by residual inhibition indicates that a group II mGluR agonist would be effective for temporarily suppressing tinnitus in the subject, further comprising administering a therapeutically effective amount of a group II mGluR agonist to a subject in which tinnitus is suppressed by residual inhibition.

10. The method of claim 9, wherein the use of residual inhibition to suppress tinnitus in the subject is tested by administering a masking stimulus using a sound synthesizer.

11. The method of claim 9, wherein the group II mGluR agonist is LY354740 or an LY354740 prodrug, or a pharmaceutically acceptable salt thereof.

12. The method of claim 1, wherein administration of the group II mGluR agonist provides suppression of tinnitus for up to 2 hours following administration.

13. The method of claim 1, wherein a dose ranging from 0.001 mg/kg to 30 mg/kg body weight of the mGluR agonist is administered to the subject.

* * * * *